(12) United States Patent
Lu

(10) Patent No.: US 12,400,734 B2
(45) Date of Patent: Aug. 26, 2025

(54) ESTIMATING PHARMACOKINETIC PARAMETERS USING DEEP LEARNING

(71) Applicant: Genentech, Inc., South San Francisco, CA (US)

(72) Inventor: James Lu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 268 days.

(21) Appl. No.: 17/950,966

(22) Filed: Sep. 22, 2022

(65) Prior Publication Data
US 2023/0119698 A1 Apr. 20, 2023

Related U.S. Application Data

(63) Continuation of application No. PCT/US2021/023788, filed on Mar. 23, 2021.

(60) Provisional application No. 62/993,639, filed on Mar. 23, 2020.

(51) Int. Cl.
G16H 70/40 (2018.01)
G06N 3/08 (2023.01)
G16B 15/30 (2019.01)
G16B 40/20 (2019.01)

(52) U.S. Cl.
CPC .............. *G16B 15/30* (2019.02); *G06N 3/08* (2013.01); *G16B 40/20* (2019.02); *G16H 70/40* (2018.01)

(58) Field of Classification Search
None
See application file for complete search history.

(56) References Cited

U.S. PATENT DOCUMENTS

| 2003/0078761 A1 | 4/2003 | Young et al. |
| 2005/0216200 A1 | 9/2005 | Urquidi-Macdonald et al. |
| 2011/0225112 A1 | 9/2011 | Cameron et al. |
| 2019/0156933 A1* | 5/2019 | Varshney ................. G06N 3/08 |

(Continued)

FOREIGN PATENT DOCUMENTS

| JP | 2020/504763 A | 2/2020 |
| JP | 2022/526937 A | 5/2022 |

(Continued)

OTHER PUBLICATIONS

Jones et al.: "Basic Concepts in Physiologically Based Pharmacokinetic Modeling in drug Discovery and Development"; Aug. 14, 2013 (Year: 2013).*

(Continued)

*Primary Examiner* — John A Pauls
(74) *Attorney, Agent, or Firm* — Baker Botts L.L.P.

(57) ABSTRACT

A method and system for predicting at least one pharmacokinetic parameter of an agent administered to a subject. One or more processors train, by one or more processors, a neural network based on a simulated training data collection. The simulated training data collection comprising a simulated time-series concentration dataset and a simulated value for a pharmacokinetic parameter that corresponds to the simulated time-series concentration dataset. The one or more processors receive a time-series concentration dataset of the agent obtained from a subject. The one or more processors predict a value for the pharmacokinetic parameter using the time-series concentration dataset and the neural network that has been trained.

11 Claims, 16 Drawing Sheets

(56) References Cited

U.S. PATENT DOCUMENTS

2019/0259474 A1     8/2019    Wang et al.
2020/0311527 A1*   10/2020   Tang ..................... G06N 3/044

FOREIGN PATENT DOCUMENTS

WO    WO-2018/085256 A1    5/2018
WO    WO-2020/198132 A1    10/2020

OTHER PUBLICATIONS

Yartsev, Alex; "Single and multiple compartment models of drug distribution"; Sep. 9, 2017 (Year: 2017).*

Mould et al.: "Basic Concepts in Population Modeling, Simulation, and Model-Based Drug Development—Part 2: Introduction to Pharmacokinetic Modeling Methods"; Apr. 17, 2013 (Year: 2013).*

Ching, T. et al. (2018). "Opportunities and obstacles for deep learning in biology and medicine," *Journal of the Royal Society Interface* 15:20170387.

Durisova, M. et al. (May 2005). "New mathematical methods in pharmacokinetic," modeling, *Basic Clin Pharmacol Toxicol* (96):335-342.

Huttunen, J.M.J. et al. (Aug. 15, 2019). "Pulse transit time estimation of aortic pulse wave velocity and blood pressure using machine learning and simulated training data," *PLoS Comput Biol* 15(8):e1007259.

International Search Report mailed on Jun. 25, 2021 for PCT Application No. PCT/US2021/023788, filed Mar. 23, 2021, 4 pages.

Niel, O. et al. (Aug. 2018, e-published May 18, 2018). "Artificial intelligence improves estimation of tacrolimus area under the concentration over time curve in renal transplant recipients," Transplant International 31(8):940-941.

Ren, B. et al. (2009). "[Prediction of mycophenolic acid exposure in renal transplantation recipients by artificial neural network]," *Acta Pharmaceutica Sinica* 44(12): 1397-1401. (English translation of abstract provided).

Written Opinion mailed on Jun. 25, 2021 for PCT Application No. PCT/US2021/023788, filed Mar. 23, 2021, 7 pages.

* cited by examiner

ESTIMATING PHARMACOKINETIC PARAMETERS USING DEEP LEARNING

The present application is a continuation of International Application No. PCT/US2021/023788, filed Mar. 23, 2021, and entitled, "Estimating Pharmacokinetic Parameters Using Deep Learning," which claims priority to U.S. Provisional Application No. 62/993,639, filed Mar. 23, 2020, and entitled "Estimating Pharmacokinetic Parameters," the entirety of each of which is incorporated by reference herein.

FIELD

This description is generally directed towards systems and methods for estimating or predicting pharmacokinetic properties for therapeutics. More specifically, there is a need for machine learning-based systems and methods for accurately estimating or predicting pharmacokinetic properties for therapeutics that are administered to patients are disclosed herein.

BACKGROUND

The development of new drugs (e.g., therapeutics) is driven by progress in many disciplines. Such disciplines include drug discovery, biotechnology, and in vivo and in vitro pharmacological/toxicological characterization techniques. Before a new therapeutic can move from a molecule or protein in the laboratory to become a new product in the hospital/clinic or local pharmacy, various questions must be answered with respect to the efficacy, administration, safety, and side effects associated with the therapeutic. Answering these types of questions typically involves a series of clinical trials, which are carefully designed to study the various facets of a new drug candidate.

Pharmacokinetics (PK) and pharmacodynamics (PD) are scientific disciplines associated with therapeutic development that typically involve mathematical modeling. In popular terms, PK (or pK) is often described as "what the body does to the drug" and PD (or pD) as "what the drug does to the body." More specifically, PK may focus on modeling how the body acts on the drug once it is administered and is subjected to the four bodily processes of absorption, distribution, metabolism and elimination or excretion (ADME). This may be accomplished by modeling concentrations in the body generally or in various areas of the body as a function of time. PD aims at linking these modeled drug concentrations to certain drug effects through a PD-model specifically designed to evaluate those effects. PK/PD modeling may thus link systemic drug concentration kinetics to the resulting drug effects over time. Such modeling enables the description and prediction of the time course of various physiological effects (e.g., tumor cell count, platelet count, neutrophil count, etc.) in response to various dosage regimens.

Conventional mathematical modeling methodologies for PK/PD evaluation may require iterations of model evaluation and refinement, with human judgement involved in various steps within the loop. This can be time and labor intensive. Examples of such existing mathematical algorithms include expectation-maximization, genetic algorithms, and scatter search. These techniques may be optimization-based, which in practice may mean that the scientist creating the model performs many function and gradient evaluations involving significant trial-and-error. Accordingly, effectively using these existing mathematical techniques to model PK and PD involves a significant amount of know-how and computational time. The know-how prerequisite and computational resource requirement represent significant obstacles along the path towards the broad adoption of PK, PD, and PK/PD modeling for non-expert users.

SUMMARY

In one or more embodiments, a method is provided for predicting at least one pharmacokinetic parameter of an agent administered to a subject. One or more processors train, by one or more processors, a neural network based on a simulated training data collection. The simulated training data collection comprising a simulated time-series concentration dataset and a simulated value for a pharmacokinetic parameter that corresponds to the simulated time-series concentration dataset. The one or more processors receive a time-series concentration dataset of the agent obtained from a subject. The one or more processors predict a value for the pharmacokinetic parameter using the time-series concentration dataset and the neural network that has been trained.

In one or more embodiments, a system is provided for predicting at least one pharmacokinetic parameter of an agent administered to a subject. The system comprises a data store for storing a time-series concentration dataset of the agent obtained from a subject; a computing device communicatively connected to the data store, and a display system communicatively connected to the computing device. The computing device comprises a pharmacokinetic data simulation engine and a pharmacokinetic prediction engine. The pharmacokinetic data simulation engine is configured to generate a simulated training data collection of one or more agents. The simulated training data collection comprises a simulated time-series concentration dataset and a simulated value for a pharmacokinetic parameter that corresponds to the simulated time-series concentration dataset. The pharmacokinetic prediction engine is configured to train a neural network using the simulated training data collection and predict a value for the pharmacokinetic parameter based on the time-series concentration dataset using the neural network that has been trained. The display system is configured to display a report containing the value predicted for the pharmacokinetic parameter.

In one or more embodiments, a method is provided for training a neural network to predict at least one pharmacokinetic parameter of an agent. One or more processors receive a simulation parameter for a compartmental-based pharmacokinetic model. The one or more processors generate a simulated training data collection using the compartmental-based pharmacokinetic model. The simulated training data collection comprises a simulated time-series concentration dataset of one or more agents and a simulated value for a pharmacokinetic parameter that corresponds to the simulated time-series concentration dataset. The compartmental-based pharmacokinetic model is encoded with the received simulation parameters. The one or more processors then train a neural network with the simulated training data collection.

In one or more embodiments, a system for training a neural network to predict a pharmacokinetic parameter value of an agent is disclosed. The system includes a data store, a computing device, and a display system. The data store stores simulation parameters for a compartmental-based pharmacokinetic model. The computing device is communicatively connected to the data store and hosts a pharmacokinetic data simulation engine and a pharmacokinetic prediction engine. The pharmacokinetic data simulation engine is configured to use the compartmental-based pharmacokinetic models to generate a simulated training data collection. The simulated training data collection comprises a simulated time-series concentration dataset of one or more agents and a simulated value for a pharmacokinetic parameter that corresponds to the simulated time-series concentration dataset. The pharmacokinetic prediction engine is configured to train a neural network using the simulated training data collection.

In one or more embodiments, a method is provided for predicting at least one pharmacokinetic parameter of an agent administered to a subject. One or more processors receive a time-series concentration dataset of the agent obtained from a subject. The one or more processors predict a value for a pharmacokinetic parameter based on the time-series concentration dataset and a neural network that has been trained using a simulated training data collection.

In one or more embodiments, a system is provided for predicting at least one pharmacokinetic parameter of an agent administered to a subject is disclosed. The system includes a data store for storing a time-series concentration dataset of the agent obtained from a subject, a computing device communicatively connected to the data store, and a display system communicatively connected to the computing device. The computing device is configured to train a neural network using a simulated training data collection and predict a value for a pharmacokinetic parameter based on the time-series concentration dataset and the neural network that has been trained. The display system is configured to display a report containing the value predicted for the pharmacokinetic parameter.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 7 is a schematic diagram of a system for predicting a PK parameter value of an agent (e.g., drug, biologic, etc.) administered to a subject (i.e., patient), in accordance with various embodiments.

FIG. 10 is an exemplary flowchart showing a method for predicting a PK parameter value of an agent (e.g., drug, biologic, etc.) administered to a subject (i.e., patient), in accordance with various embodiments.

FIG. 11 are plots that demonstrates the improved accuracy of estimating AUC and $C_{max}$ using a novel NN approach versus the conventional Trapezoidal Rule, in accordance with various embodiments.

Figure 1:
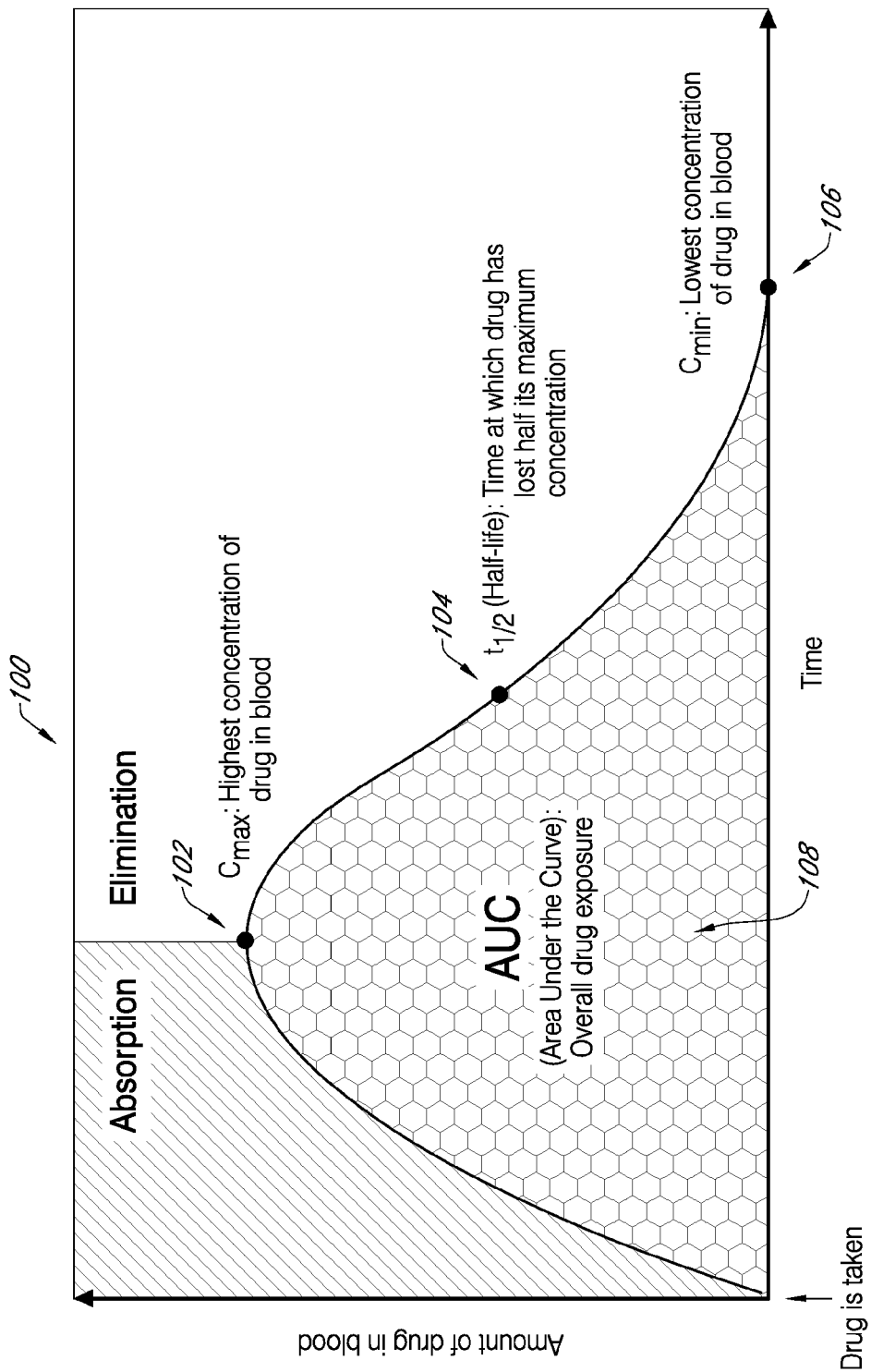
FIG. 1 is a visualization graph that depicts a standard time-series concentration plot 100 and illustrates examples of exemplary PK parameters.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

The principles of pharmacokinetics/pharmacodynamics (PK/PD) have become a well-established quantitative framework for understanding the dose-concentration-effect relationships of various therapeutics and selecting the proper protocols (e.g., dosage, schedules, etc.) for such therapeutics. Current methods for estimating pharmacokinetics properties (e.g., as described below in Section III) are rudimentary. For example, some currently available methods use a non-compartmental analysis (NCA) approach that numerically infers pharmacokinetic parameters. One such method estimates the area under the curve (AUC) formed by the amount of a therapeutic in a subject's blood over time. The AUC can be computed using the Trapezoidal Rule in which the AUC is computed as a sum of trapezoids. These types of approaches are simple and fast.

However, such currently available methodologies may be inaccurate in various situations as their accuracy relies on crucial assumptions or presumptions. These presumptions include, for example, that all the relevant measurements are available and that the time intervals between the measurements are appropriately short and condensed. Therefore, approximation of the AUC using the Trapezoidal Rule can lead to limitations with respect to the accuracy with which pharmacokinetic parameters are estimated. Further, estimation variability of the linear trapezoidal rule strongly depends on data completeness. If missing interim values are imputed by means of linear interpolation, large amounts of missing values will lead to a decreasing estimation accuracy.

Thus, recognizing and taking into account the above-described issues, the specification describes various exemplary embodiments of systems and methods for accurately estimating or predicting pharmacokinetic properties for therapeutics that are administered to patients. It should be appreciated, however, that although the systems and methods disclosed herein refer to their application in pharmacokinetics specifically, they are equally applicable to other analogous fields such as toxicokinetics and toxicodynamics.

The embodiments described herein provide methods and systems for predicting pharmacokinetic parameters with a higher level of accuracy when compared to conventional methods. Using machine learning (ML) or deep learning (DL) helps enable this improved accuracy with pharmacokinetic modeling. For example, with a deep learning system (e.g., comprising one or more neural network models), predictions of pharmacokinetic parameters are driven by learning features of the underlying data. Further, a deep learning system enables exploitation of local patterns in data to make inferences. Further, with a deep learning system, as the amount of data used for training the deep learning system increases, the prediction accuracy of the deep learning system increases.

In various embodiments, a method is provided for applying one or more mathematical models to generate simulated data; training one or more machine learning (ML) or deep learning (DL) algorithms (e.g., convolutional neural network, etc.) with the simulated PK data for one or more existing or potential future agents (e.g., chemical therapeutic or toxin, biologic therapeutic or toxin, etc.); and generating predictions or providing estimates of one or more PK parameters (e.g., AUC, $C_{max}$, $T_{max}$, $t_{1/2}$, etc.) using real-life (e.g., clinical) PK data.

In various embodiments, a system for predicting or estimating PK parameters can include a data store for storing measured (or "real-life"/clinical) PK data and one or more computers/servers that can host and execute software code that comprises a PK data simulation engine and a PK prediction engine. The PK data simulation engine can be configured to apply one or more mathematical models to simulate PK data that can be used to train ML or DL algorithms. The PK prediction engine can be configured to train the ML or DL algorithms, using the simulated PK data, to make predictions or estimates of PK parameters using the measured PK data stored in the data store.

II. Definitions

The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the phrase "Area Under the Curve" (AUC) may refer to an area of a curve that describes the variation of a therapeutic (drug) concentration in subject blood plasma as a function of time post administration.

As used herein, the phrase "Maximum Concentration" ($C_{max}$) may refer to a maximum (or peak) serum concentration that a therapeutic (drug) achieves in a specified compartment or test area of the body after the drug has been administrated and before the administration of a second dose.

As used herein, the phrase "Minimum Concentration" ($C_{min}$) or "Trough Concentration" ($C_{through}$) may refer to a minimum (or peak) serum concentration that a therapeutic (drug) achieves in a specified compartment or test area of the body after the drug has been administrated and before the administration of a second dose.

As used herein, the term "Time of Maximum Concentration" ($T_{max}$) may refer to a time when a maximum concentration is reached after a therapeutic (drug) dose is administered and before the next dose is administered.

As used herein, the term "Half-life" ($t_{1/2}$) may refer to a time that it takes for a concentration of a therapeutic (drug) in blood plasma to reach one-half of its steady-state value.

As used herein, the term "mean residence time" (MRT) may refer to an average time that a therapeutic (drug) stays at the site of action.

As used herein, the phrase "compartmental model" or "compartment modelling" may refer to mathematical modelling techniques used for predicting PK parameters (indicative of the ADME) of synthetic or natural therapeutic (drug) in a test subject by modelling concentrations of the therapeutic in different areas of the body. Within these mathematical models, the different areas of the body can be divided into parts, called compartments, where the therapeutic can be assumed to behave in the same manner.

As used herein, the phrase "non-compartmental model" (NCA) may refer to model-independent techniques (meaning they do not rely upon assumptions about body compartments) used for predicting PK parameters (indicative of the ADME) of a therapeutic (drug) administered to a test subject. NCA enables the computation of PK parameters of a therapeutic (drug) from the time course of measured drug concentrations.

As used herein, a "biologic" or "large molecule therapeutic" may refer to proteins and other biological macromolecules that have a therapeutic effect.

As used herein, "therapeutics compound" or "small molecule therapeutic" may refer to any organic compound that affects a biologic process with a relatively low molecular weight, below 900 Daltons.

As used herein, an "artificial neural network" or "neural network" (NN) may refer to mathematical algorithms or computational models. Neural networks can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

A neural network may process information in two ways; when it is being trained it may be in "learning mode" and when it puts what it has learned into practice it may be in "inference (or prediction) mode." Neural networks may learn through a feedback process called backpropagation which allows the network to adjust the weight factors (modifying its behavior) of the individual nodes in the intermediate hidden layers so that the output matches the outputs of the training data. In other words, a neural network may receive training data (learning examples) and automatically learn how to reach the correct output, even when it is presented with a new range or set of inputs. Examples of the types of neural networks, include, but are not limited to: Feedforward Neural Network (FNN), Recurrent Neural Network (RNN), Modular Neural Network (MNN), Convolutional Neural Network (CNN), Residual Neural Network (ResNet), etc.

III. Conventional Methods For Predicting PK Parameters

FIG. 1 is a visualization graph that depicts a standard time-series concentration plot 100 and illustrates examples of typical PK parameters. As shown herein, the various types of PK parameters (e.g., $C_{max}$ 102, $t_{1/2}$ 104, $C_{min}$ 106, AUC 108, etc.) are depicted on time-series concentration plot 100 for a drug after the drug has been administered to a test subject. $C_{max}$ 102 is a value that is indicative of the highest concentration of the drug in the test subject's blood. It is often of importance to know the maximum concentration, $C_{max}$ 102, of a drug in the blood and the time it takes to reach this maximum, $T_{max}$. For an intravenous bolus dose, the maximum concentration is obtained just after the drug is injected into the bloodstream, that is $T_{max}=0$. In the case of extravascular (oral) administration, the concentration will not peak until after a while because of the absorption step. In general, the time it takes to reach the maximum can be found by differentiating the expression for C(t) for the system, with respect to t, set the derivative equal to zero and finally solve for $T_{max}$.

In plot 100, $t_{1/2}$ 104 or half-life represents the biological half-life of the drug in the test subject after administration. That is, the half-life of a drug is the time at which the drug has lost half its maximum concentration. $C_{min}$ 106 is the lowest concentration of the drug in the blood post administration. This PK parameter is oftentimes used in bioavailability and bioequivalence studies.

AUC 108 or "Area Under the Curve" is a value that is indicative of the test subject's overall therapeutics exposure. AUC 108 can be evaluated using most types of models (compartmental or non-compartmental) and can be determined graphically based of a time-series of concentration measurements.

Figure 2:
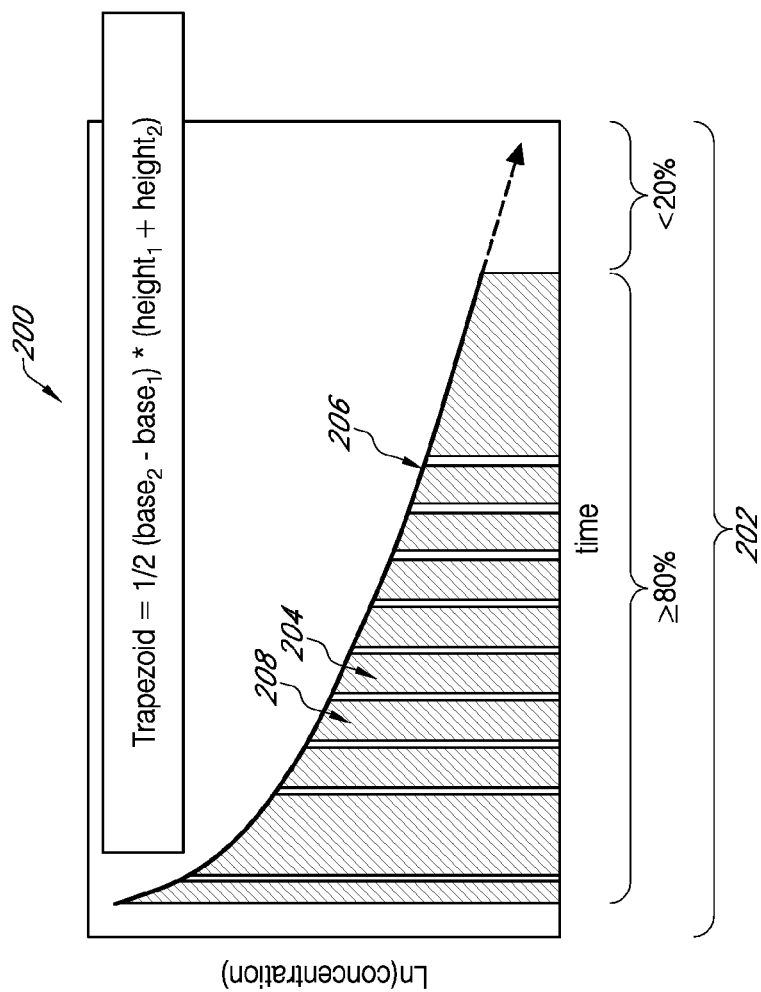
FIG. 2 is an illustration of a time-series concentration plot.

FIG. 2 is an illustration of a time-series concentration plot 200. As shown herein, time-series concentration plot 200 includes time-series concentration data 202 that is measured from blood samples drawn from a test subject at various time intervals that occur after the administration of a drug. The AUC 204 for time-series concentration plot 200 is comprised of a series can be estimated using the conventional "Trapezoidal Rule" whereby the AUC 204 under the times series concentration plot 200 is mathematically subdivided into a series of AUC segments 208, which are trapezoids, that are bracketed by the time intervals at which the drug concentration is measured. The AUC 204 is computed as a sum-of-trapezoids calculation.

Figure 3:
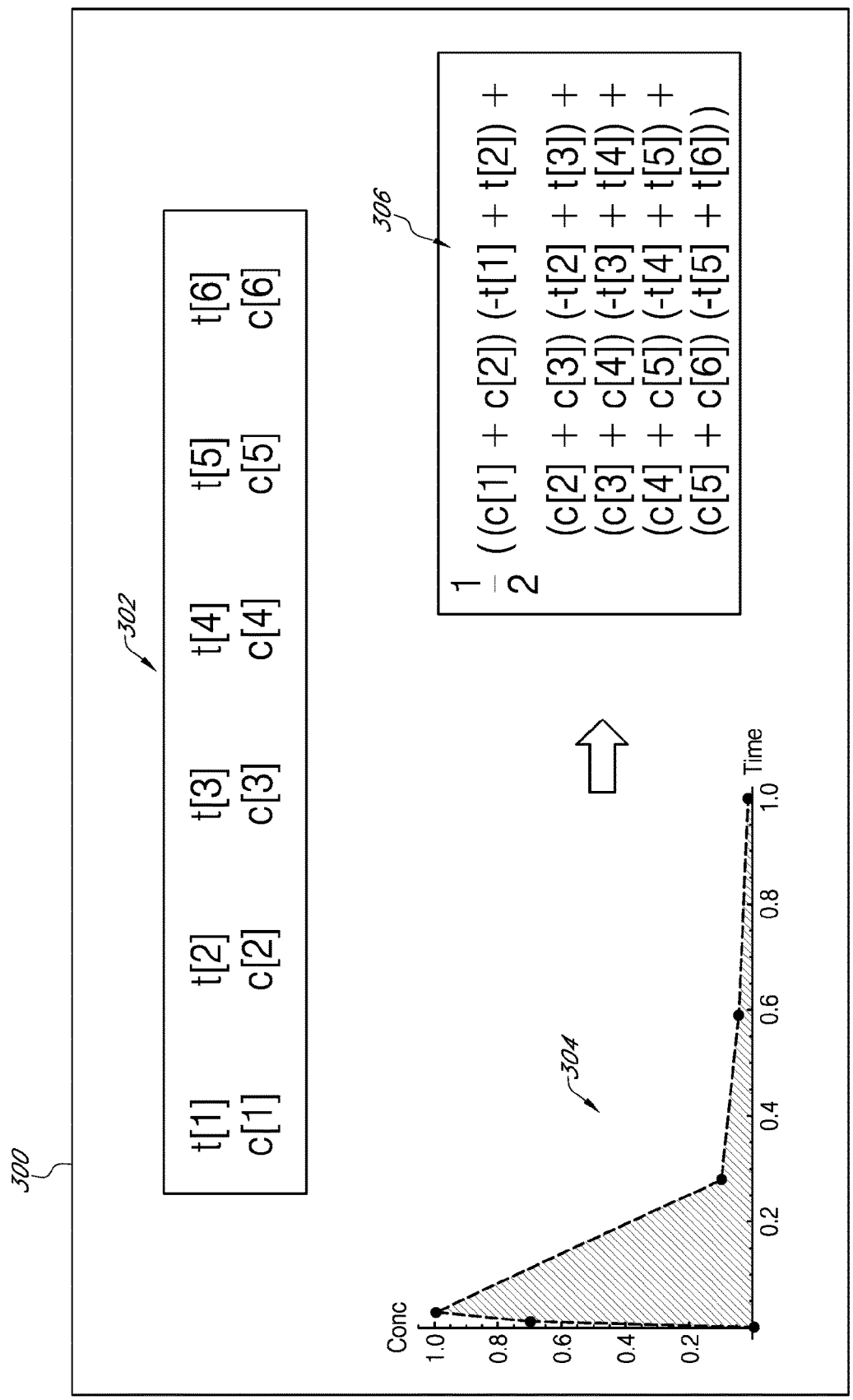
FIG. 3 is an illustration of a workflow for the sum-of-trapezoids calculation performed for the time-series concentration plot in FIG. 2.

FIG. 3 is an illustration of a workflow 300 for the sum-of-trapezoids calculation performed for the time-series concentration plot 200 in FIG. 2. Data 302 includes the time points at which concentration measurements were generated. Plot 304 represents a trapezoid-based representation of time-series concentration plot 200 in FIG. 2 in which AUC 204 is divided into a series of trapezoids. Formula 306 identifies one manner in which the sum-of-trapezoids calculation can be performed to provide an estimation of the AUC. Thus, this AUC estimation is based on an approximation of the entire area by means of summing up individual subareas. This method of numerical integration generally assumes that the trajectory is partitioned until the last observation $t_n$ in n-1 sections.

While this conventional approach is simple and can be fast, its accuracy relies on crucial presumptions that all the relevant measurements are available and that the time intervals between the measurements are appropriately short and condensed. Thus, as previously described, this type of approach has limitations with respect to its accuracy.

IV. Estimation of PK Parameters Using Deep Learning Neural Networks

In contrast to the accuracy-impaired methods described in Section III, the various embodiments of the present disclosure provide methods and systems for accurately predicting one or more pharmacokinetic parameter values for an agent that is administered to a subject. These methods and systems can be implemented via computer software, hardware, firmware, or a combination thereof.

Figure 4:
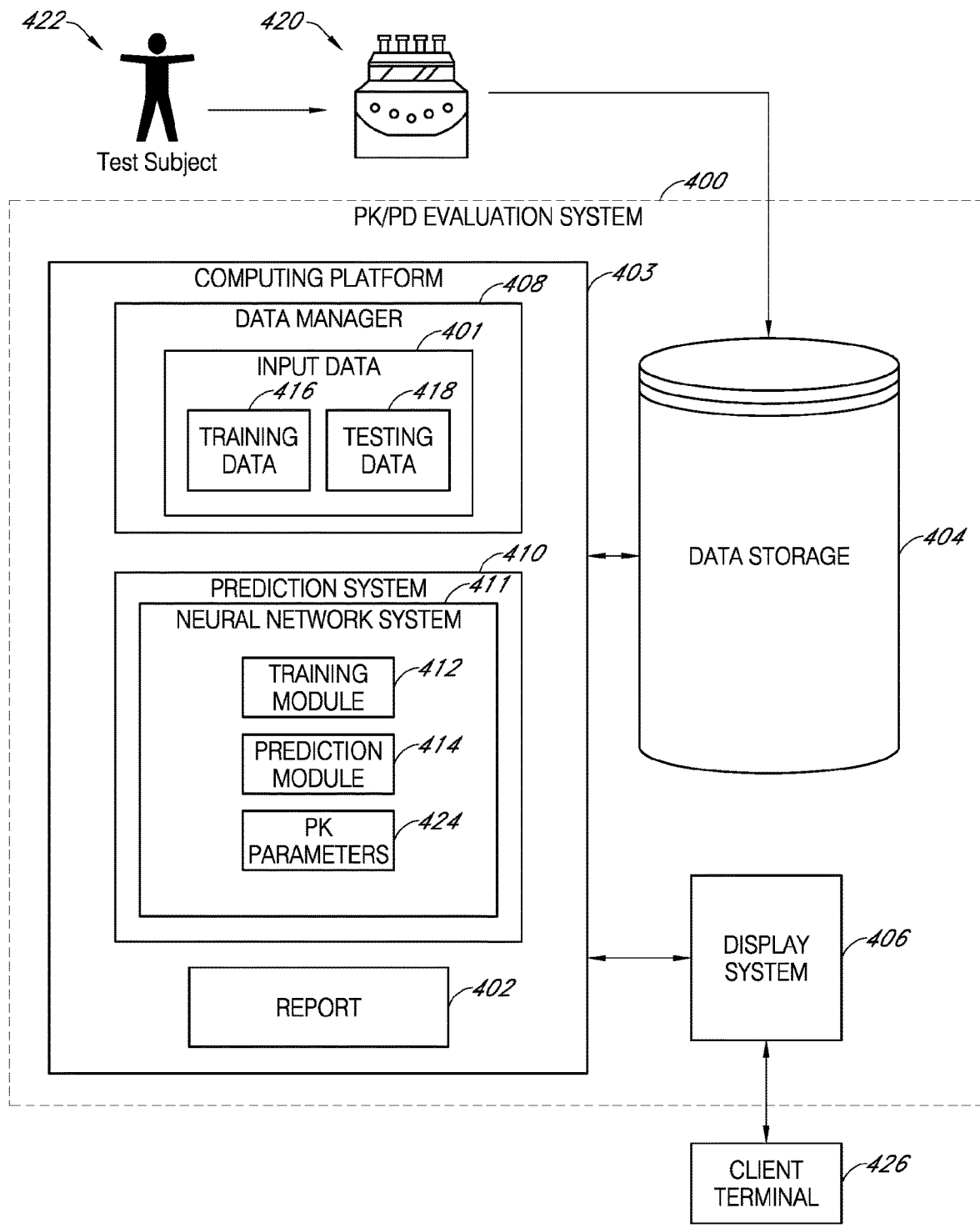
FIG. 4 is a block diagram of a pharmacokinetic (PK) evaluation system 400 in accordance with one or more example embodiments.

FIG. 4 is a block diagram of a pharmacokinetic (PK) evaluation system 400 in accordance with one or more example embodiments. PK evaluation system 400 may be used to evaluate PK effects resulting from the administration of a drug (e.g., therapeutic). In various embodiments, PK evaluation system 400 is trained based on observed data and then used to predict PK effects over time (including time beyond that for which observed data is provided or available). As previously described, a PK effect is a dose effect or an effect of the body on the drug in the body (e.g., drug concentration).

PK evaluation system 400 may be used in various settings including, but not limited to, a research setting, clinical trial setting, a drug development setting, a hospital setting, or in some other type of setting. PK evaluation system 400 may receive and process input data 401 to generate a report 402 that describes and/or contains information based on these PK. Input data 401 may include, for example, lab measurements taken from the plasma of subjects, measurements from continuous monitoring devices (e.g., in hospital or home settings), or some other type of data. The report 402 may include, for example, a PK time course that is predicted for a certain number of days or weeks into the future based on a current dosing regimen. In some cases, report 402 may also include at least one of a corresponding PK time course that is predicted based on certain dosing interruptions and/or adjustments to the current dosing regimen. Report 402 may be generated for an individual subject in question or for the entire cohort of subjects in a clinical trial. In one or more examples, report 402 may include one or more recommended actions based on a predicted PK time course.

PK evaluation system 400 includes computing platform 403, data storage 404, and display system 406. Computing platform 403 may take various forms. In one or more embodiments, computing platform 403 includes a single computer (or computer system) or multiple computers in communication with each other. In other examples, computing platform 403 takes the form of a cloud computing platform. In some embodiments, computing platform 403 is referred to as a computing device/analytics server. In some embodiments, computing platform 403 can be a workstation, mainframe computer, distributed computing node (part of a "cloud computing" or distributed networking system), personal computer, mobile device, etc.

Data storage 404 and display system 406 are each in communication with computing platform 403. Data storage 404 may communicatively connected to computing platform 403 in various ways such as, but not limited to, a network connection that can be either a "hardwired" physical network connection (e.g., Internet, LAN, WAN, VPN, etc.) or a wireless network connection (e.g., Wi-Fi, WLAN, etc.).

In some examples, data storage 404, display system 406, or both may be considered part of or otherwise integrated with computing platform 403. Thus, in some examples, computing platform 403, data storage 404, and display system 406 may be separate components in communication with each other, but in other examples, some combination of these components may be integrated together.

PK evaluation system 400 includes data manager 408 and prediction system 410 implemented in the computing platform 403. Each of the data manager 408 and the neural network system 410 is implemented using hardware, software, firmware, or a combination thereof. Data manager 408 may also be referred to as a pharmacokinetic (PK) data simulation engine. Prediction system 410 may also be referred to as a pharmacokinetic (PK) prediction engine.

It should be appreciated that the various components or engines of PK evaluation system 400 can be combined or collapsed into a single engine, component, or module, depending on the requirements of the particular application or system architecture. Moreover, in various embodiments, data storage 404, data manager 408, prediction system 410 or a combination thereof may comprise additional engines or components as needed by the particular application or system architecture.

In various embodiments, the data manager 408 provides input data 401 to the neural network system 410. This input data 401 may be retrieved from the data storage 404, received from some other source, or a combination thereof. The input data 401 may have been generated via one or more samples from one or more subjects. For example, a sample analyzer 420 can be communicatively connected to data storage 404 via one or more communications links (e.g., via a serial bus, a wireless network connection, etc.). Sample analyzer 420 can be configured to analyze blood samples from a test subject, such as test subject 422, and determine the concentration of an agent (drug or biologic) in the blood. Time-series concentration data can be generated as blood samples are drawn from the subject 422 at set time intervals and analyzed using the sample analyzer 420. In various embodiments, the time-series concentration data can then be stored in the data storage 404 for subsequent processing. In some embodiments, the time-series concentration data is fed as input data 401 to data manager 408 in real-time or near real-time.

Prediction system 410 is a machine learning or deep learning prediction system. In one or more embodiments, prediction system 410 includes a neural network system 411. The neural network system 411 includes one or more neural network models.

When the neural network system 410 is being trained, the input data 401 takes the form of training data 416. After training, the neural network system 410 may be used in practice to predict PK parameters and in these examples, the input data 401 may be referred to as testing data 418. Thus, the type of input data 401 provided to the neural network system 410 may take different forms depending on whether the neural network system 410 is in a training mode or in a prediction mode.

For example, the neural network system 410 may include a training module 412 and a prediction module 414. The training module 412 may be used when the neural network system 410 is being trained (e.g., in a training mode). As one example, the training module 412 trains the neural network system 410 using training data 416 received from the data manager 408. The prediction module 414 uses the neural network system 410 for prediction (e.g., in a prediction mode). For example, after the neural network system 410 has been trained, the prediction module 414 may be used in practice to predict PK parameters 424 using testing data 418 received from the data manager 408.

In some embodiments, data manager 408 simulates training data 416 used by prediction system 410. For example, data manager 408 may be configured to use one or more compartmental-based pharmacokinetic models to generate training data 416 (e.g., a simulated training data collection). Training data 416 (the simulated training data collection) can be comprised of a plurality of discrete simulated time-series concentration datasets of one or more modeled agents (drug or biologic) and simulated values for one or more PK parameters that correspond to the plurality of discrete simulated time-series concentration datasets. Examples of the types of simulated pharmacokinetic parameters include, but are not limited to: AUC, $C_{max}$, $C_{min}$, $C_{trough}$, $T_{max}$, MRT, $T_{last}$, or $t_{1/2}$.

In various embodiments, the compartmental-based pharmacokinetic models can be custom configured thru the input of one or more compartmental model parameters prior to the running of the model simulation to generate the simulated time-series concentration data. Examples of compartmental model parameters include, but are not limited to: dosing scheme (e.g., subcutaneous, oral, intravenous, etc.), molecular class (i.e., small molecule or large molecule), molecular species (e.g., drug, mAbs, protein, enzyme, etc.), compartmental model specific parameters (e.g., volume of distribution for the central compartment, absorption constants, elimination constants, etc.), modeled species (e.g., mammalian, rodents, human, non-human primates, etc.), modeled species demographics (e.g., age, weight, gender etc.), baseline albumin, baseline tumor size, etc.

In various embodiments, the compartmental-based pharmacokinetic model can be a one-compartment pharmacokinetic model. For one-compartment pharmacokinetic models, the compartmental model parameters that can be set include, but are not limited to: volume of distribution for the central compartment, absorption rate into central compartment, elimination rate from the central compartment, etc.

In various embodiments, the compartmental-based pharmacokinetic model can be a two-compartment model. For two-compartment models, the compartmental model parameters that can be set include, but are not limited to: volume of distribution for the central compartment, volume of distribution for the peripheral compartment, absorption rate into central compartment, elimination rate from the central compartment, inter-compartmental clearance between central and peripheral compartments, etc.

In various embodiments, the compartmental-based pharmacokinetic model can be a Michaelis-Menten two-compartment model. For Michaelis-Menten PK two-compartment models, the compartmental model parameters that can be set include, but are not limited to: volume of distribution for the central compartment, volume of distribution for the peripheral compartment, absorption rate into central compartment, elimination rate from the central compartment, inter-compartmental clearance between central and peripheral compartments, Michaelis-Menton constants associated with the non-linear clearance mechanism, etc.

In various embodiments, training data 416 is sent in real-time or near real-time to prediction system 410 for use in training neural network system 411. In various embodiments, training data 416 is generated and stored in data storage 404 and then subsequently sent/retrieved to train neural network system 411.

Prediction system 410, in some embodiments, can be configured to initialize a self-organizing neural network, to train the neural network using training data 416 and predict one or more PK parameters 424 based on the time-series concentration dataset of the agent obtained from the subject (and stored in data storage unit 706). Examples of the types of predicted OK parameters include, but are not limited to: AUC, $C_{max}$, $C_{min}$, $C_{trough}$, $T_{max}$, MRT, $T_{last}$, or $t_{1/2}$.

After the values for PK parameters 424 have been predicted, PK parameters 424 can be displayed as report 402 (e.g., a result or summary) on display system 406. Display system 406 in some embodiments may be implemented at a client terminal 426 that is communicatively connected to computing platform 403. In various embodiments, client terminal 426 can be a thin client computing device. In various embodiments, client terminal 426 can be a personal computing device having a web browser (e.g., INTERNET EXPLORER™, FIREFOX™, SAFARI™, etc.) that can be used to control the operation of data storage 404, data manager 408, prediction system 410, or a combination thereof.

Figure 5:
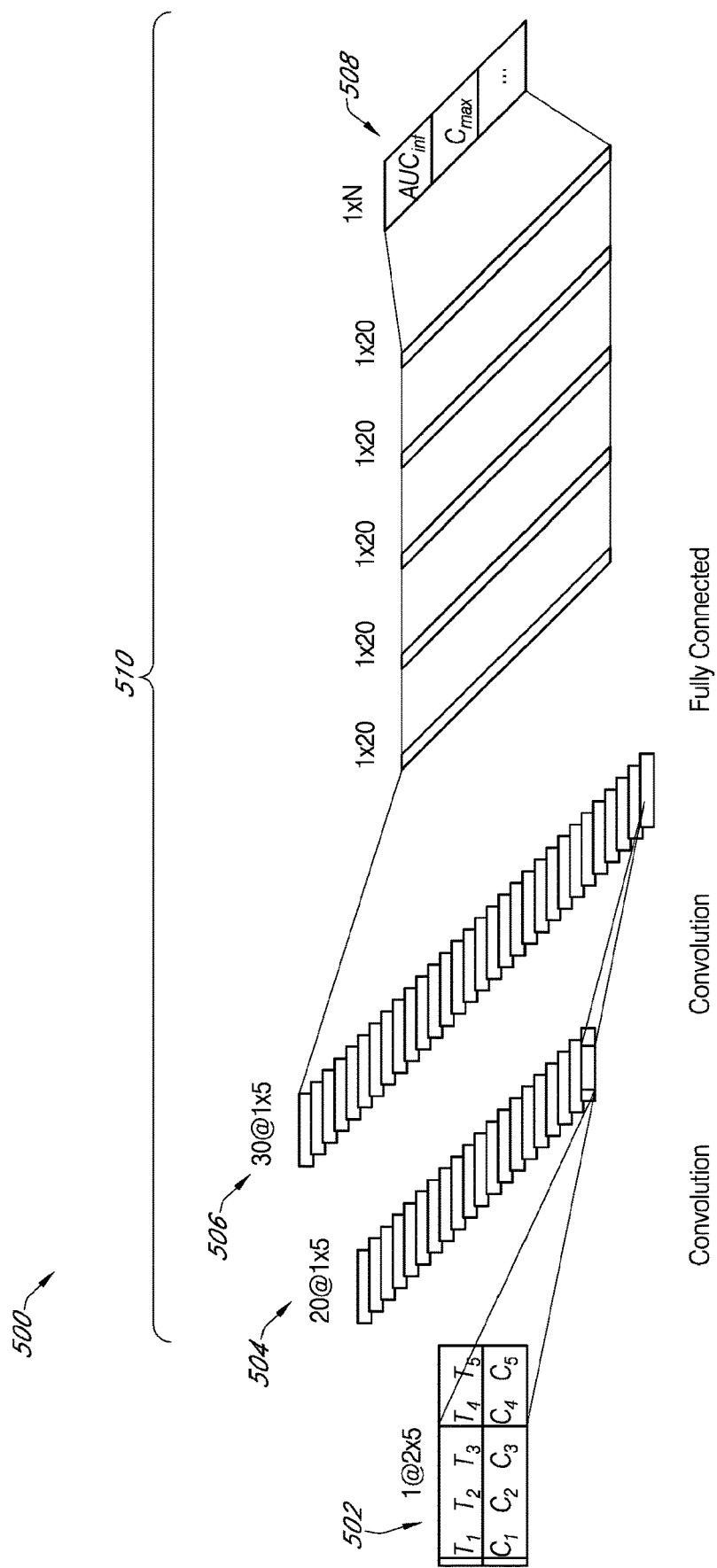
FIG. 5 is a depiction of an exemplary NN system and how it can be used to process time-series concentration data to predict PK parameters, in accordance with various embodiments.

FIG. 5 is a depiction of an exemplary NN system 500 and how it can be used to process time-series concentration data to predict PK parameters, in accordance with various embodiments. The NN system 500 shown in FIG. 5 can perform a ML-based methodology for PK parameter estimation or prediction whereby a NN model 510 is trained by a plurality of simulated PK training datasets (i.e., simulated time-series concentration data and their corresponding PK parameters) generated by PK compartmental model simulations and NCA modelling so as to enable the automation of NCA PK parameter modelling tasks by the trained NN model 510. In various embodiments, the NN model 510 is a Feedforward Neural Network. In various embodiments, the NN model 510 is a Recurrent Neural Network. In various embodiments, the NN model 510 is a Modular Neural Network. It should be understood, however, that essentially any type of NN model 510 topology can be employed as long as it is capable of being trained by simulated PK training datasets to output accurate estimates or predictions of PK parameters 508 when fed real-life (not simulated) or real-time time-series concentration data 502.

In various embodiments, the NN model 510 is a Deep Learning NN model which is a class of machine learning algorithms that uses multiple (hidden) layers to progressively extract higher level features from the raw input. In various embodiments, the DL NN model is a Convolutional Neural Network. In various embodiments, the DL NN model is a Residual Neural Network.

As shown in FIG. 5, a NN model 510 can be comprised of an input layer 504, one or more hidden layers 506 and an output layer 508. In various embodiments, the input layer 504 is configured to ingest times series concentration data 502 so that the data can be processed by the NN model 510. In various embodiments, the input layer 504 can be configured to ingest additional inputs besides time-series concentration data, such as, but not limited to: the therapeutic (agent) being modeled, subject demographic information, disease status, etc.

In various embodiments, the hidden layers 506 can be comprised of 2 or more, 5 or more, 4 or more, 5 or more, or greater than 5 layers of nodes. In various embodiments, the number of hidden layers 506 and/or the number of nodes in each hidden layer 506 (in the NN 510 model) is preset prior to training. In various embodiments, the number of hidden layers 506 and/or the number of nodes in each hidden layer 506 (in the NN 510 model) is automatically set by the NN model 510 when it is being trained.

In various embodiments, the output layer 508 can be configured to output one or more types of PK parameters including, but not limited to: AUC, $C_{max}$, $C_{min}$, $C_{trough}$, $T_{max}$, MRT, $T_{last}$, or $t_{1/2}$.

At a high level, NN model 510 operates by finding the correct mathematical manipulation (through "learning" using training data) to turn the input, either the input layer of input data or any a preceding layer, into the output of a subsequent layer, either the output layer of the output of the NN model 510 or the output of any given layer which will serve as the preceding layer to another layer. This occurs regardless of whether the mathematical manipulation is a linear relationship or a non-linear relationship. The NN model 510 "learns" by adjusting the weights (and optional thresholds) of the nodes in the various layers of the NN model to improve the accuracy of the result. Learning is complete when examining additional observations (of training data) does not usefully reduce the error rate or reduces the error rate to some pre-defined value. Complex NN models have many layers, hence the name "deep learning" neural networks.

After learning (training) and during model use (inference, prediction), the NN model 510 serves to relate an input layer l input set of data to an output layer l output set of data via a mathematical function and the previously trained weights. During inference, the weights are fixed and the input data and numerical values of the weights together with the architecture of the layers of the NN model 510 (as introduced above), represent the mathematical function of how the input data and weights are computed together to calculate the outputs of the NN model 510.

Figure 6:
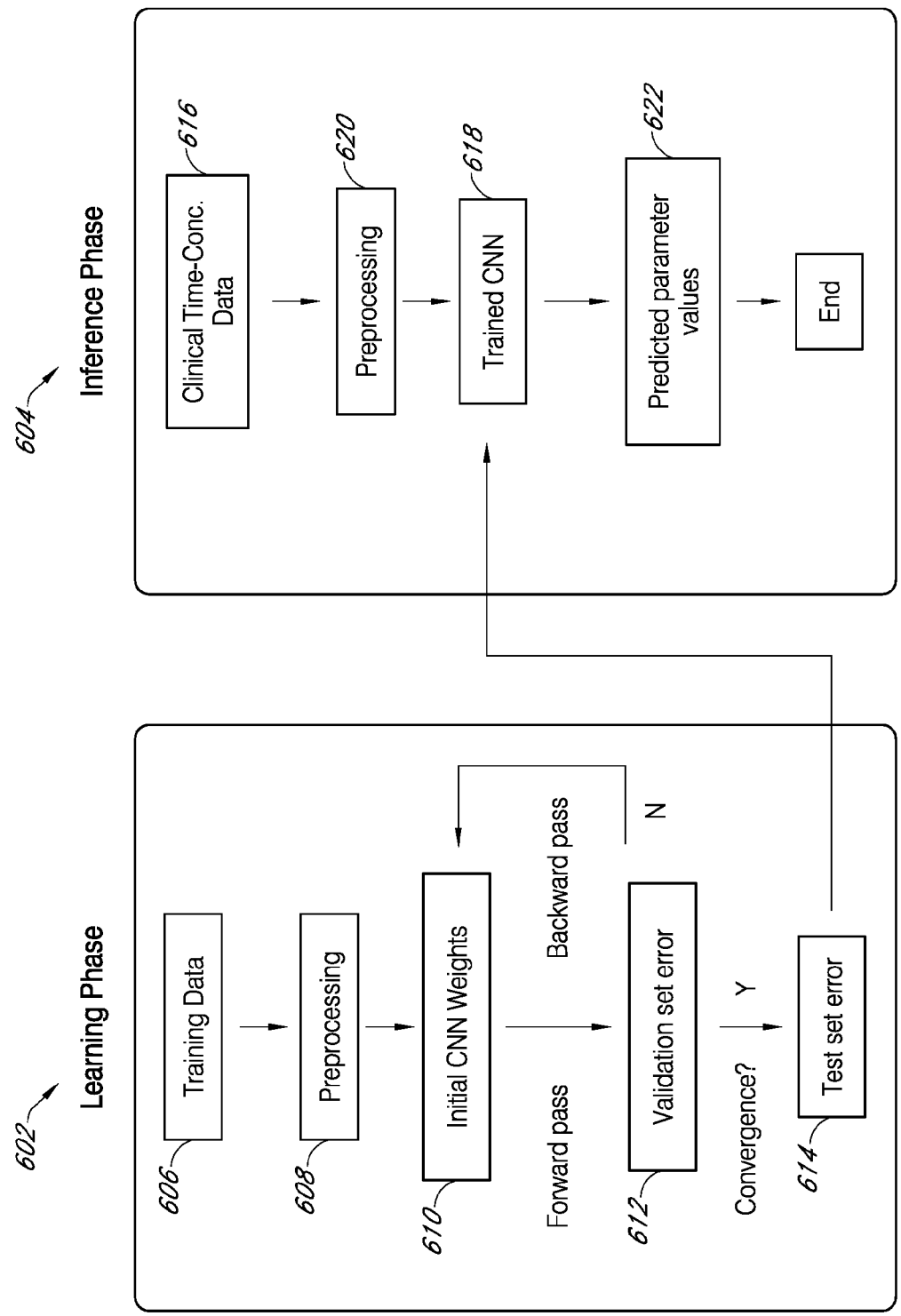
FIG. 6 illustrates an exemplary high-level workflow of how a NN model can be trained during a learning phase and then puts what it has learned into practice to predict PK parameters, in accordance with various embodiments.

FIG. 6 illustrates an exemplary high-level workflow of how a NN model can be trained during a learning phase and then puts what it has learned into practice to predict PK parameters, in accordance with various embodiments. As discussed above, neural network processes information in two ways; when it is being trained it is in a learning phase 602 and when it puts what it has learned into practice it is in an inference phase 604.

As shown herein, during the learning phase 602, training data 606 is first preprocessed 608 and then it is iteratively fed into the NN model 610 through a backpropagation (which is one method of training) process that adjusts the weights (and optional thresholds) of the nodes in each of the various layers of the NN model 610 such that it converges to a predetermined (or preset) validation set error value 612 and/or test set error value 614.

In various embodiments, the preprocessing 608 of the training data 606 is a normalization of the time-series concentration data and the correlated NCA PK parameters that make up the training data 606. In various embodiments, the preprocessing 608 of the training data. 606 filters out poor-quality datasets from the training data 606.

After the backpropagation process cycles through enough iterations such that the validation set error value 612 and the test set error value 614 converges to predetermined (preset) values, the fully trained NN model 618 can be used in the inference phase 604. In the inference phase 604, the clinically obtained time-series concentration data 616 (i.e., real-world clinical data) goes through a pre-processing step 620 and then this preprocessed data is fed to the trained NN model 618, which processes the preprocessed data and outputs one or more predicted. PK parameter values 622. The outputs can be PK parameters such as, but not limited to: AUC, $C_{max}$, $C_{min}$, $C_{trough}$, $T_{max}$, MRT, $T_{last}$, or $t_{1/2}$.

In various embodiments, the preprocessing 608 of the training data 606 is a normalization of the time-series concentration data and the correlated NCA PK parameters that make up the training data 606. In various embodiments, the preprocessing 608 of the training data 606 filters out poor-quality datasets from the training data 606.

Figure 7:
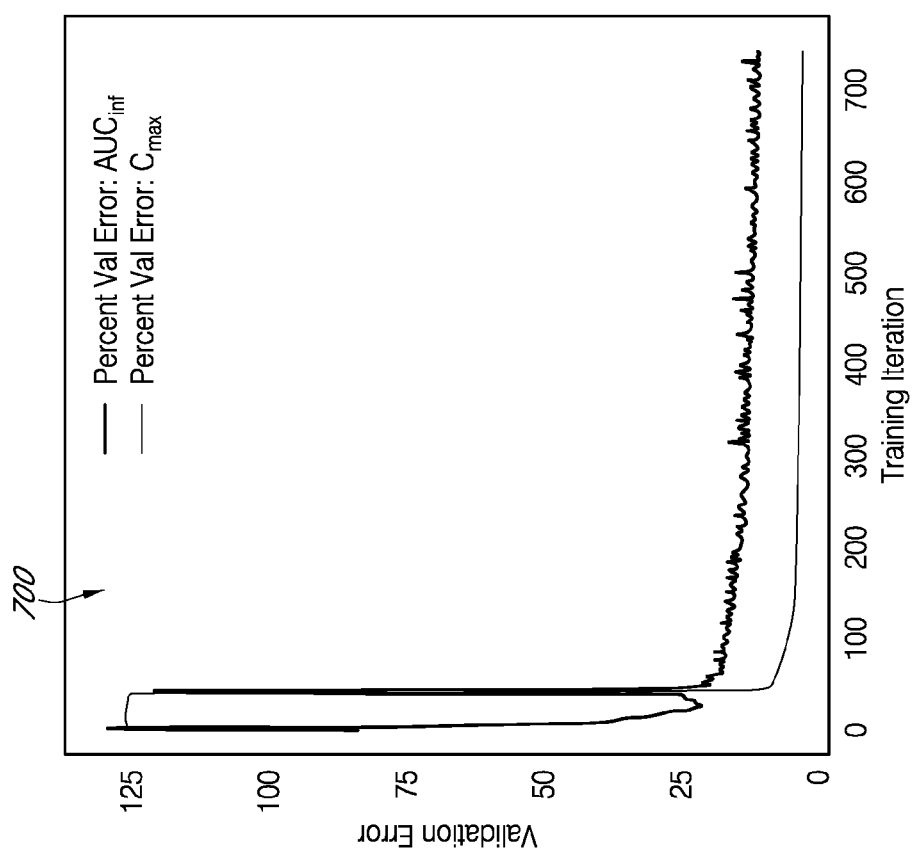
FIG. 7 is an illustration of a plot showing percent validation error in accordance with an example embodiment.

FIG. 7 is an illustration of a plot 700 showing percent validation error in accordance with an example embodiment. Plot 700 shows how the percent validation error, which is calculated as the predicted value versus actual value after running a validation dataset through NN model 610 during the training phase 602, for predicted $AUC_{inf}$ and $C_{max}$ values decreases as the number of training iterations increases. It should be noted, however, that the improvements to the accuracy of the predictions eventually levels off as a function of the number of training iterations which suggests that that there is an optimal number of training iterations for NN model 610 and that there is a diminishing return in prediction accuracy when its surpassed.

During the backpropagation process, the "forward pass" refers to the calculation process whereby the values of the output layer is calculated from the input data. The input data traverses through all nodes from the first to last layer. A loss function is calculated from the output values and then "backward pass" refers to the process of counting changes in weights (de facto learning), using a gradient descent algorithm (or similar). Computation is made from last layer, backward to the first layer. A backward and forward pass cycle together makes one iteration.

Figure 8:
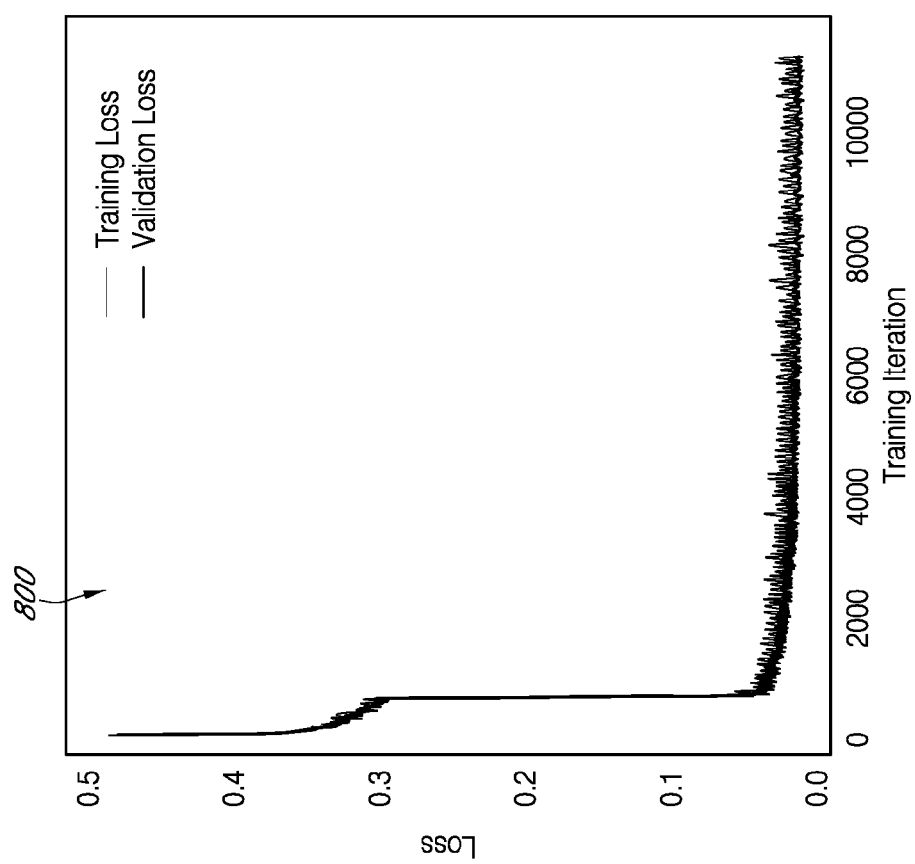
FIG. 8 is an illustration of a plot showing an example of training and validation loss as a function of the number of training iterations in accordance with an example embodiment.

FIG. 8 is an illustration of a plot 800 showing an example of training and validation loss as a function of the number of training iterations in accordance with an example embodiment. Plot 800 shows training and validation loss with respect to the initial NN model 610 and fully trained NN model 618 in FIG. 6. Training loss is the error on the training set of data. Validation loss is the error after running the validation set of data through the trained network. Generally, the lower the loss, the better a model (unless the model has over-fitted to the training data). The loss is an interpretation as to how well the NN model 610 is doing for these two sets. Unlike accuracy, loss is not a percentage. It is a summation of the errors made for each example in training or validation sets.

Figure 9:
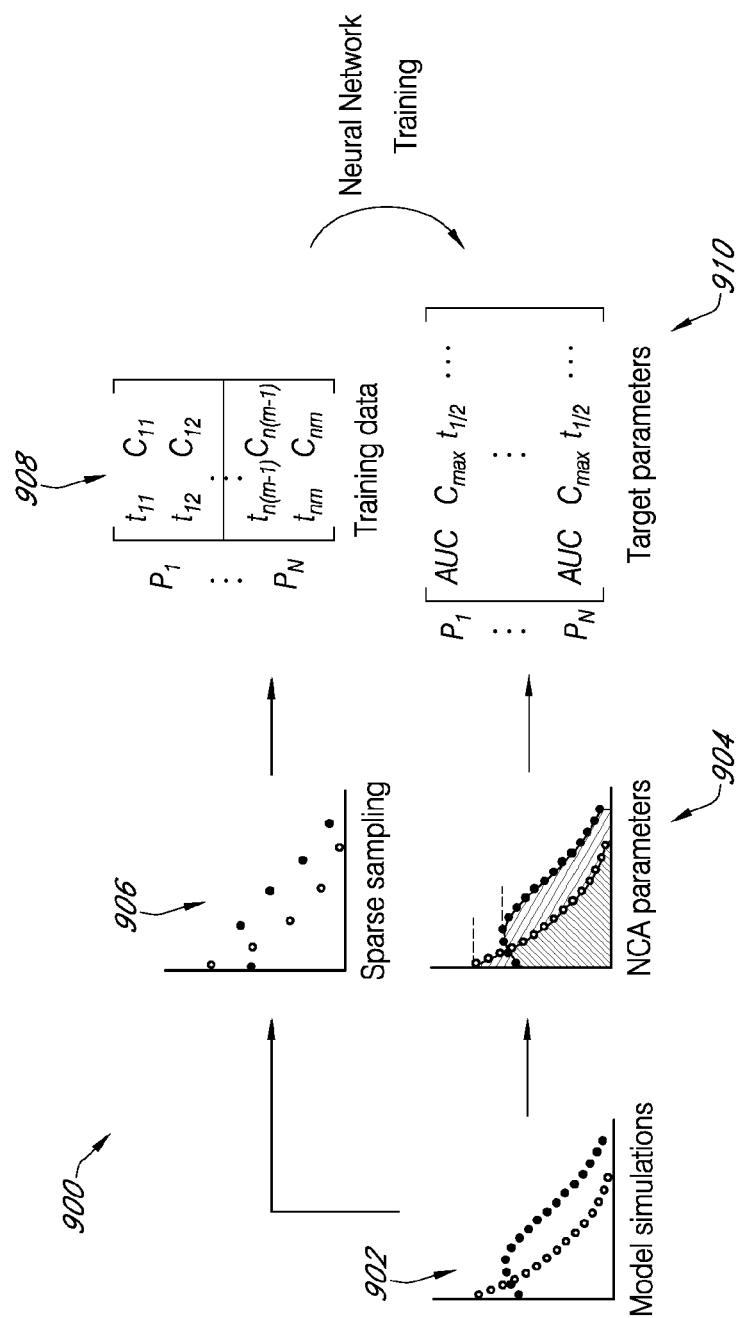
FIG. 9 is an illustration of an example training workflow in accordance with various embodiments.

FIG. 9 is an illustration of an example training workflow 900 in accordance with various embodiments. Training workflow 900 is a high-level illustration of how simulated PK data can be generated and used to create training datasets.

As depicted herein, simulated time-series concentration data 902 is generated using one or more types of PK compartmental models. This involves first setting (by inputting) one or more PK compartmental model simulation parameters and then running the PK compartmental model simulation to generate simulated time-series concentration data 902 for one or more existing or potential future therapeutic agents.

Examples of PK compartmental model simulation parameters include, but are not limited to: dosing scheme (e.g., subcutaneous, oral, intravenous, etc.), molecular class (e.g., small molecule or large molecule), molecular species (e.g., drug, mAbs, protein, enzyme, etc.), compartmental model specific parameters (e.g., volume of distribution for the central compartment, absorption constants, elimination constants, etc.), modeled species (e.g., mammalian, rodents, human, non-human primates, etc.), modeled species demographics (e.g., age, weight, gender etc.), baseline albumin, baseline tumor size, etc.

In various embodiments, a one-compartment model can be used to simulate the time-series concentration data 902. For PK one-compartment models, the compartmental parameters that can be set include, but are not limited to: volume of distribution for the central compartment, absorption rate into central compartment, elimination rate from the central compartment, etc.

In various embodiments, a two-compartment model can be used to simulate the time-series concentration data 902. For PK two-compartment models, the compartmental parameters that can be set include, but are not limited to: volume of distribution for the central compartment, volume of distribution for the peripheral compartment, absorption rate into central compartment, elimination rate from the central compartment, inter-compartmental clearance between central and peripheral compartments, etc.

In various embodiments, a Michaelis-Menten PK two-compartment model can be used to simulate the time-series concentration data 902. For Michaelis-Menten PK two-compartment models, the compartmental parameters that can be set include, but are not limited to: volume of distribution for the central compartment, volume of distribution for the peripheral compartment, absorption rate into central compartment, elimination rate from the central compartment, inter-compartmental clearance between central and peripheral compartments, Michaelis-Menton constants associated with the non-linear clearance mechanism, etc.

After the simulated time-series concentration data 902 is generated, it is sparsely sampled 906 to form a subset of simulated time-series concentration training datasets 908 and each of the simulated time-series concentration training datasets 908 is further processed using non-compartmental analysis (NCA) 904 to calculate their corresponding simulated PK parameter values 910. Examples of the types of simulated PK parameter values include, but are not limited to: AUC, $C_{max}$, $C_{min}$, $C_{trough}$, $T_{max}$, MRT, $T_{last}$, or $t_{1/2}$.

Figure 10:
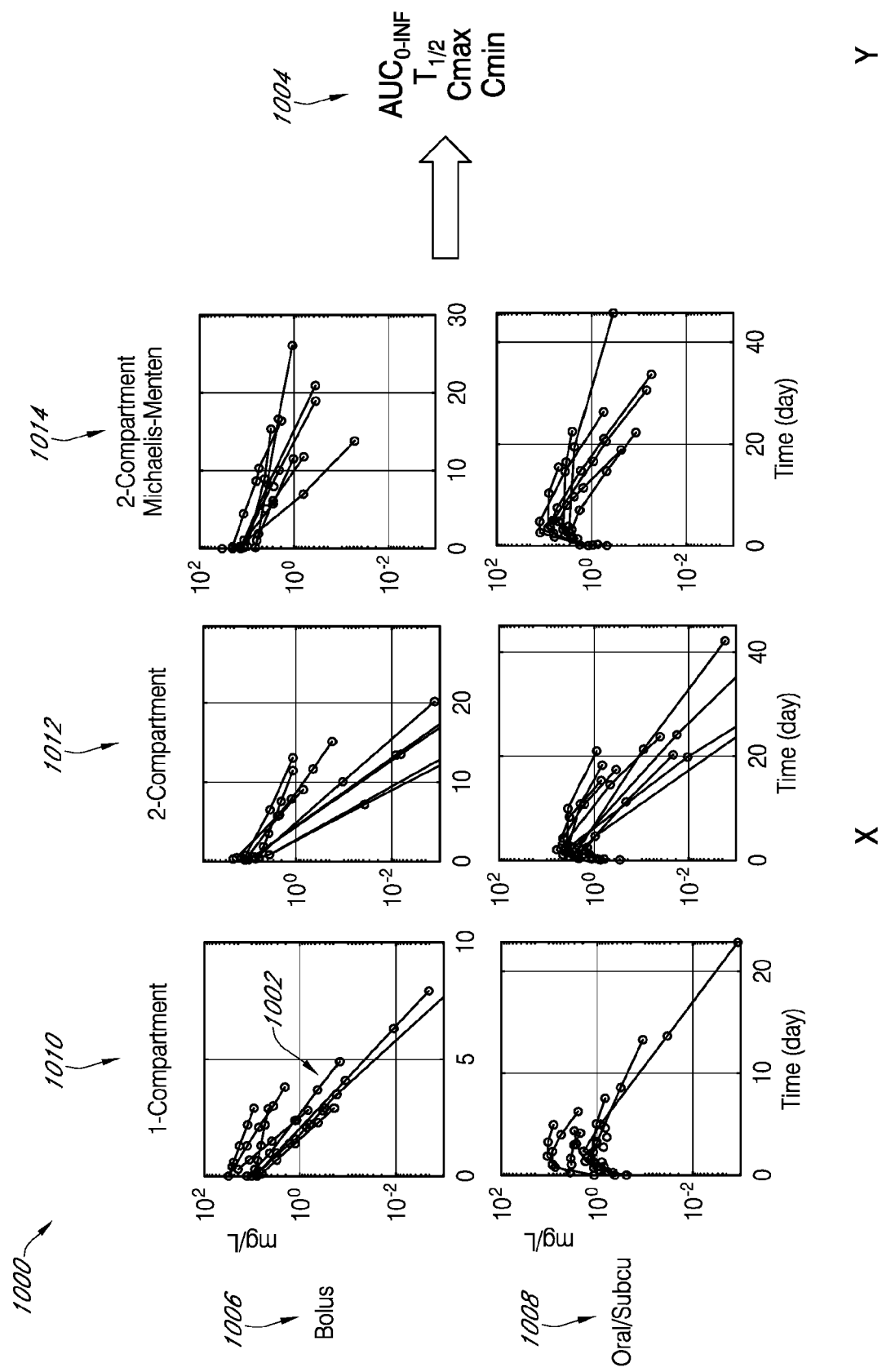
FIG. 10 is an illustration of a series of plots for various forms of compartment modeling in accordance with various embodiments.

FIG. 10 is an illustration of a series of plots 1000 for various forms of compartment modeling in accordance with various embodiments. Series of plots 1000 illustrate how compartmental modeling can be used to simulate time-series concentration data that is coupled with PK parameters predicted using NCA to form training datasets, in accordance with various embodiments.

In the example illustrated in FIG. 10, three different compartmental models (i.e., 1-Compartment 1010, 2-Compartment 1012 and 2-Compartment Michaelis-Menten 1014) were used to generate simulated time-series concentration datasets 1002. The same compartmental model simulations were run using different therapeutic dosing scheme settings (i.e., bolus 1006 and oral/subcutaneous 1008) to illustrate the effects of dosing scheme on the simulated time-series concentration datasets 1002.

As discussed above, after the simulated time-series concentration datasets 1002 are generated, they are further processed using NCA to calculate their corresponding simulated PK parameter values 1004. In various embodiments, the simulated time-series concentration datasets are of one or more existing or potential future therapeutic agents.

V. Experimental Results

The improved systems and methods, disclosed herein, were compared against conventional approaches to predicting a pharmacokinetic parameter value of an agent that is administered to a subject.

Figure 11:
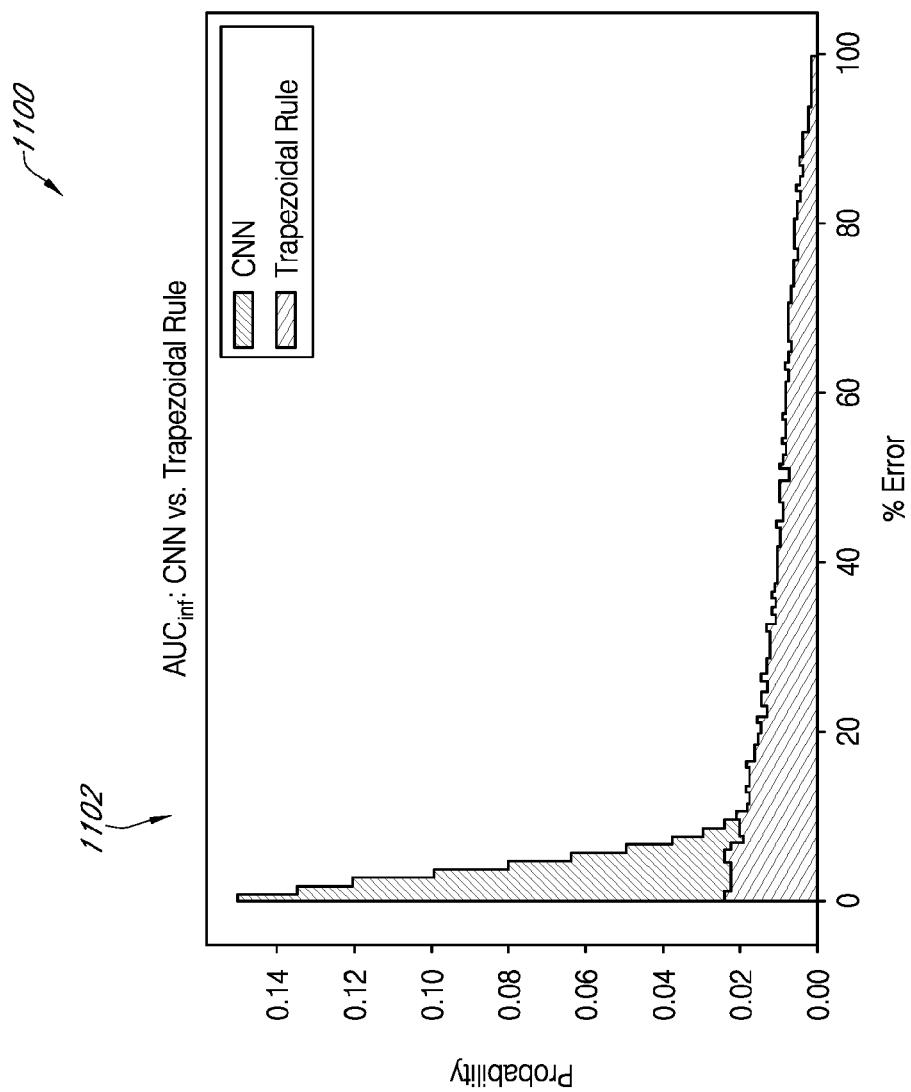
FIG. 11 illustrates a set of plots that demonstrates the improved accuracy of estimating AUC and $C_{max}$ using the neural network approach described herein as compared to the conventional Trapezoidal Rule in accordance with an example embodiment.
Figure 11:
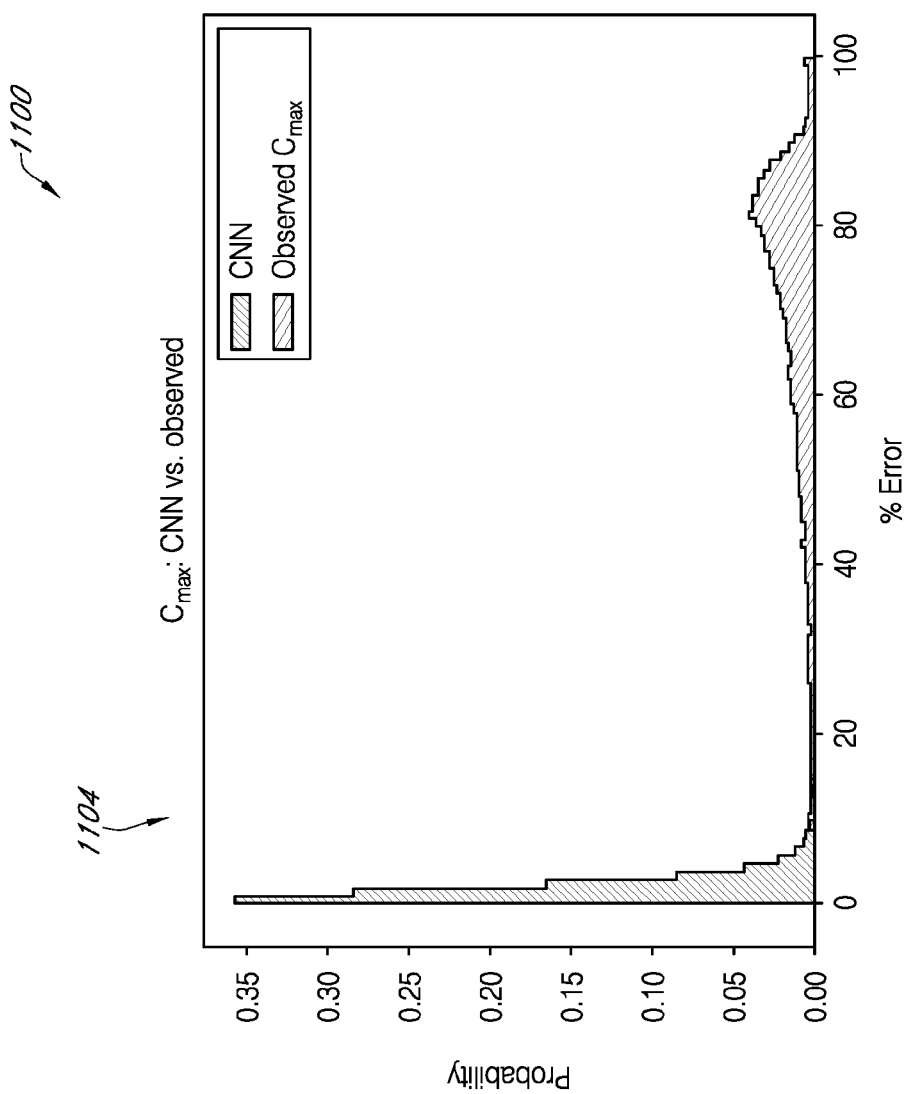

FIG. 11 illustrates a set of plots 1100 that demonstrates the improved accuracy of estimating AUC and $C_{max}$ using the neural network approach described herein as compared to the conventional Trapezoidal Rule in accordance with an example embodiment.

As shown herein, an $AUC_{inf}$% Error histogram 1102 shows a plot of % Error (predicted vs actual) for $AUC_{inf}$ values determined using the NN methods disclosed herein and the conventional Trapezoidal Rule method. It is clear both visually and numerically (mean percentage error), that the $AUC_{inf}$ values determined using the NN methods were sizeably more accurate than the $AUC_{inf}$ values determined using the conventional Trapezoidal Rule method. For example, for $AUC_{inf}$, the mean percentage error of the NN methods was about 9.1, while the Trapezoidal Rule mean percentage error was about 81.5.

The observed significant improvement in accuracy of the NN methods over conventional methods was reinforced by the $C_{max}$ % Error histogram 1104 that plots % Error for $C_{max}$ values determined using the NN methods and the conventional general observation method. This is important because this shows that the improvement in accuracy using the NN predictive methods applies to determination of all PK parameters (e.g., $C_{min}$, $C_{trough}$, $T_{max}$, or $t_{1/2}$) and not just to the determination of $AUC_{inf}$ values. For $C_{max}$, the mean percentage error for the NN methods was about 2.2 the observed versus true mean percentage error was about 88.8.

VI. Example Methods

Figure 12:
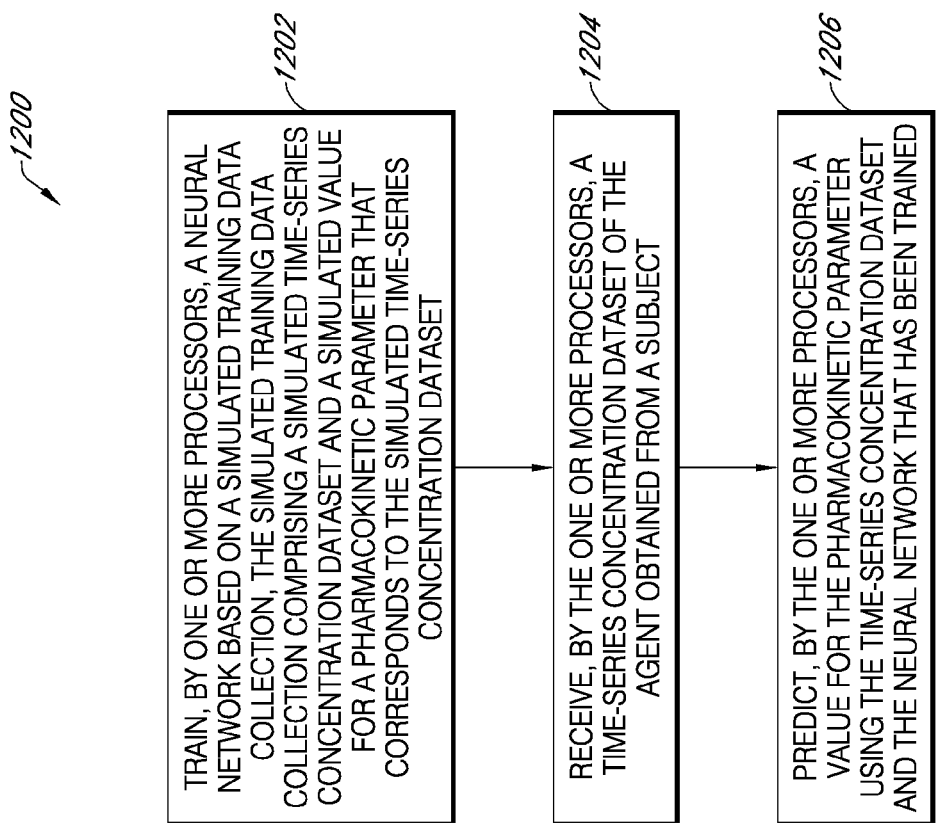
FIG. 12 is an exemplary flowchart showing a method for predicting a PK parameter value of an agent (i.e., drug or biologic) administered to a subject (i.e., patient), in accordance with various embodiments.

FIG. 12 is an exemplary flowchart showing a method 1200 for predicting a PK parameter value of an agent (i.e., drug or biologic) administered to a subject (i.e., patient), in accordance with various embodiments.

In step 1202, a neural network is trained, by one or more processors, a neural network based on a simulated training data collection, the simulated training data collection comprising a simulated time-series concentration dataset and a simulated value for a pharmacokinetic parameter that corresponds to the simulated time-series concentration dataset. In some embodiments, step 1202 includes training the neural network based on multiple discrete simulated time-series concentration datasets, which may be, in turn, used to simulate values for one or more pharmacokinetic parameters for each simulated time-series concentration dataset of the multiple discrete simulated time-series concentration datasets.

In one or more embodiments, the simulated value for the pharmacokinetic parameter corresponds to the entirety of the simulated time-series concentration dataset. In one or more embodiments, the simulated value for the pharmacokinetic parameter corresponds to a particular portion of the simulated time-series concentration dataset (e.g., one or more data points within the simulated time-series concentration dataset).

In various embodiments, the neural network is a Feedforward Neural Network (FNN). In various embodiments, the neural network is a Recurrent Neural Network (RNN). In various embodiments, the neural network is a Modular Neural Network (MNN). In various embodiments, the neural network is a Convolutional Neural Network (CNN). In various embodiments, the neural network is a Residual Neural Network (ResNet).

In various embodiments, the compartmental-based pharmacokinetic model is a one-compartment model. In various embodiments the compartmental-based pharmacokinetic model is a two-compartment model. In various embodiments, the compartmental-based pharmacokinetic model is a two-compartment Michaelis-Menten model.

In step 1204, a time-series concentration dataset of the agent obtained from a subject is received by the one or more processors. The agent may comprise, for example, a small molecule therapeutic or a biologic.

In step 1206, a value for the pharmacokinetic parameter is predicted, by the one or more processors, using the time-series concentration dataset and the neural network that has been trained. As discussed above, examples of the types of pharmacokinetic parameters for which values are predicted include, but are not limited to: AUC, $C_{max}$, $C_{min}$, $C_{trough}$, $T_{max}$, MRT, $T_{last}$, or $t_{1/2}$.

Figure 13:
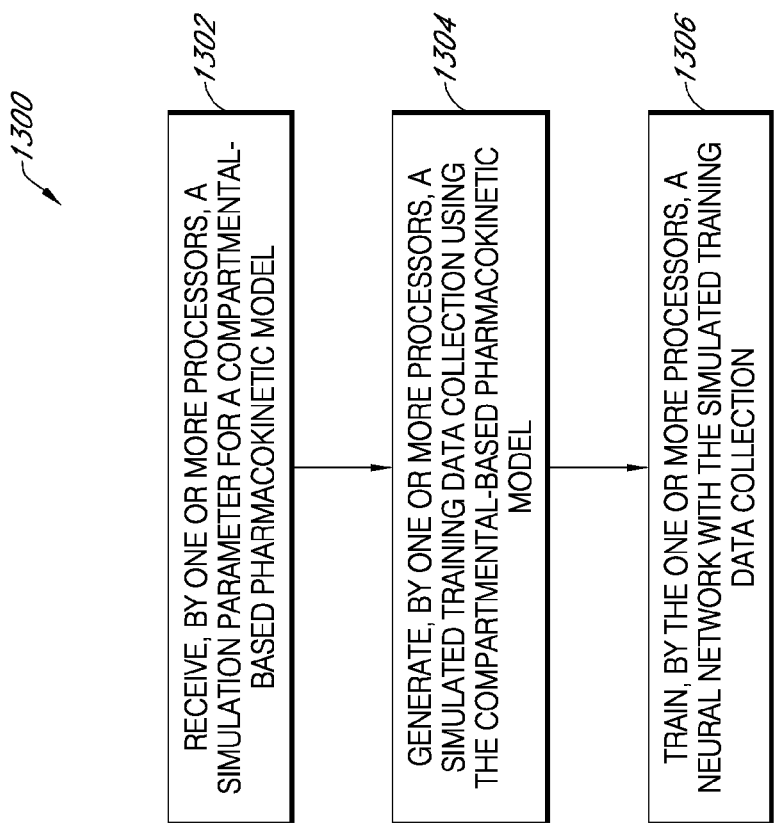
FIG. 13 is an exemplary flowchart showing a method for training a neural network to predict a pharmacokinetic parameter value of an agent (i.e., drug or biologic), in accordance with various embodiments.

FIG. 13 is an exemplary flowchart showing a method 1300 for training a neural network to predict a pharmacokinetic parameter value of an agent (i.e., drug or biologic), in accordance with various embodiments.

In step 1302, simulation parameters for a compartmental-based pharmacokinetic model are received by one or more processors. Examples of simulation parameters include, but are not limited to: dosing scheme (e.g., subcutaneous, oral, intravenous, etc.), molecular class (i.e., small molecule or large molecule), molecular species (e.g., drug, mAbs, protein, enzyme, etc.), compartmental model specific parameters (e.g., volume of distribution for the central compartment, absorption constants, elimination constants, etc.), modeled species (e.g., mammalian, rodents, human, non-human primates, etc.), modeled species demographics (e.g., age, weight, gender etc.), baseline albumin, baseline tumor size, etc.

In various embodiments, the compartmental-based pharmacokinetic model is a one-compartment model. In various embodiments the compartmental-based pharmacokinetic model is a two-compartment model. In various embodiments, the compartmental-based pharmacokinetic model is a two-compartment model with Michaelis-Menten clearance.

In step 1304, a simulated training data collection is generated, by the one or more processors, using the compartmental-based pharmacokinetic model. The simulated training data collection includes a simulated time-series concentration dataset (or a plurality of simulated time-series concentration datasets) and a simulated value for at least one pharmacokinetic parameter that corresponds to the simulated time-series concentration dataset (or the plurality of simulated time-series concentration datasets). In one or more embodiments, simulated values for the one or more pharmacokinetic parameters are generated for each simulated time-series concentration dataset of the plurality of simulated time-series concentration datasets.

The compartmental-based pharmacokinetic model is encoded with the received simulation parameters. Examples of the types of pharmacokinetic parameters for which simulated values are generated include, but are not limited to: AUC, $C_{max}$, $C_{min}$, $C_{trough}$, $T_{max}$, MRT, $T_{last}$, or $t_{1/2}$.

In step 1306, a neural network is trained, by the one or more processors, with the simulated training data collection using the one or more processors. The trained neural network may then be used to predict a pharmacokinetic parameter value of an agent.

In various embodiments, the neural network is a Feedforward Neural Network (FNN). In various embodiments, the neural network is a Recurrent Neural Network (RNN). In various embodiments, the neural network is a Modular Neural Network (MNN). In various embodiments, the neural network is a Convolutional Neural Network (CNN). In various embodiments, the neural network is a Residual Neural Network (ResNet).

Figure 14:
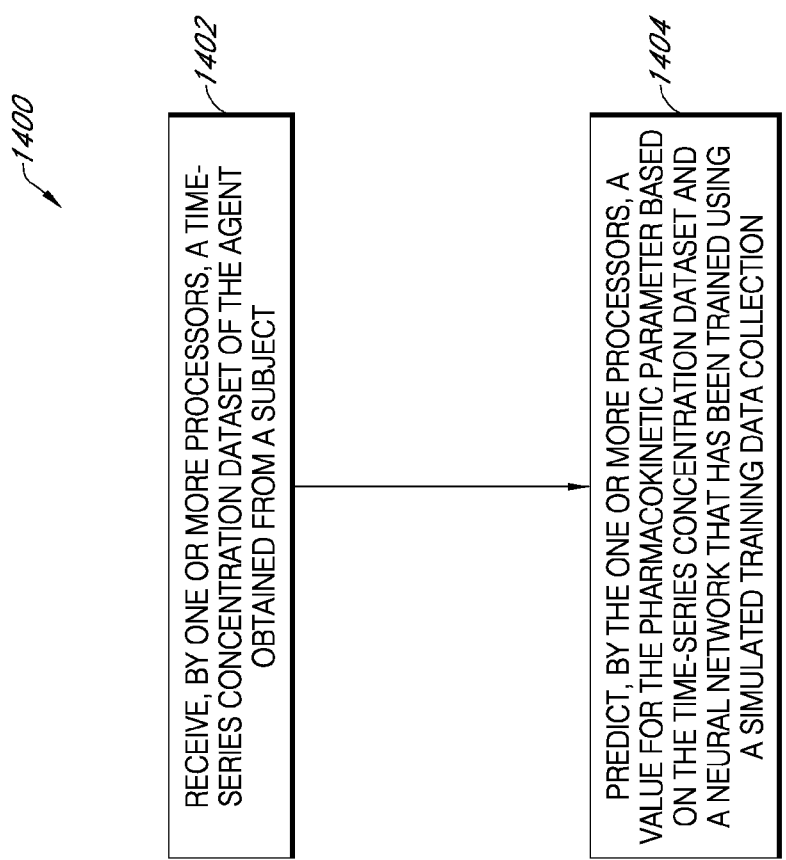
FIG. 14 is an exemplary flowchart showing a method for predicting a PK parameter value of an agent (e.g., drug, biologic, etc.) administered to a subject (i.e., patient), in accordance with various embodiments.

FIG. 14 is an exemplary flowchart showing a method 1400 for predicting a PK parameter value of an agent (e.g., drug, biologic, etc.) administered to a subject (i.e., patient), in accordance with various embodiments.

In step 1402, a time-series concentration dataset of an agent obtained from a subject is received by one or more processors.

In step 1404, a value for a pharmacokinetic parameter is predicted, by the one or more processors, based on the time-series concentration dataset and a neural network that has been trained using a simulated training data collection. The neural network may be trained via, for example, without limitation, method 1300 in FIG. 13. The neural network may be trained using a simulated training data collection comprising a plurality of simulated time-series concentration datasets of one or more agents and simulated values for one or more pharmacokinetic parameters for each simulated time-series concentration dataset of the plurality of simulated time-series concentration datasets.

In various embodiments, the neural network is a Feedforward Neural Network (FNN). In various embodiments, the neural network is a Recurrent Neural Network (RNN). In various embodiments, the neural network is a Modular Neural Network (MNN). In various embodiments, the neural network is a Convolutional Neural Network (CNN). In various embodiments, the neural network is a Residual Neural Network (ResNet).

VII. Computer-Implemented System

Figure 15:
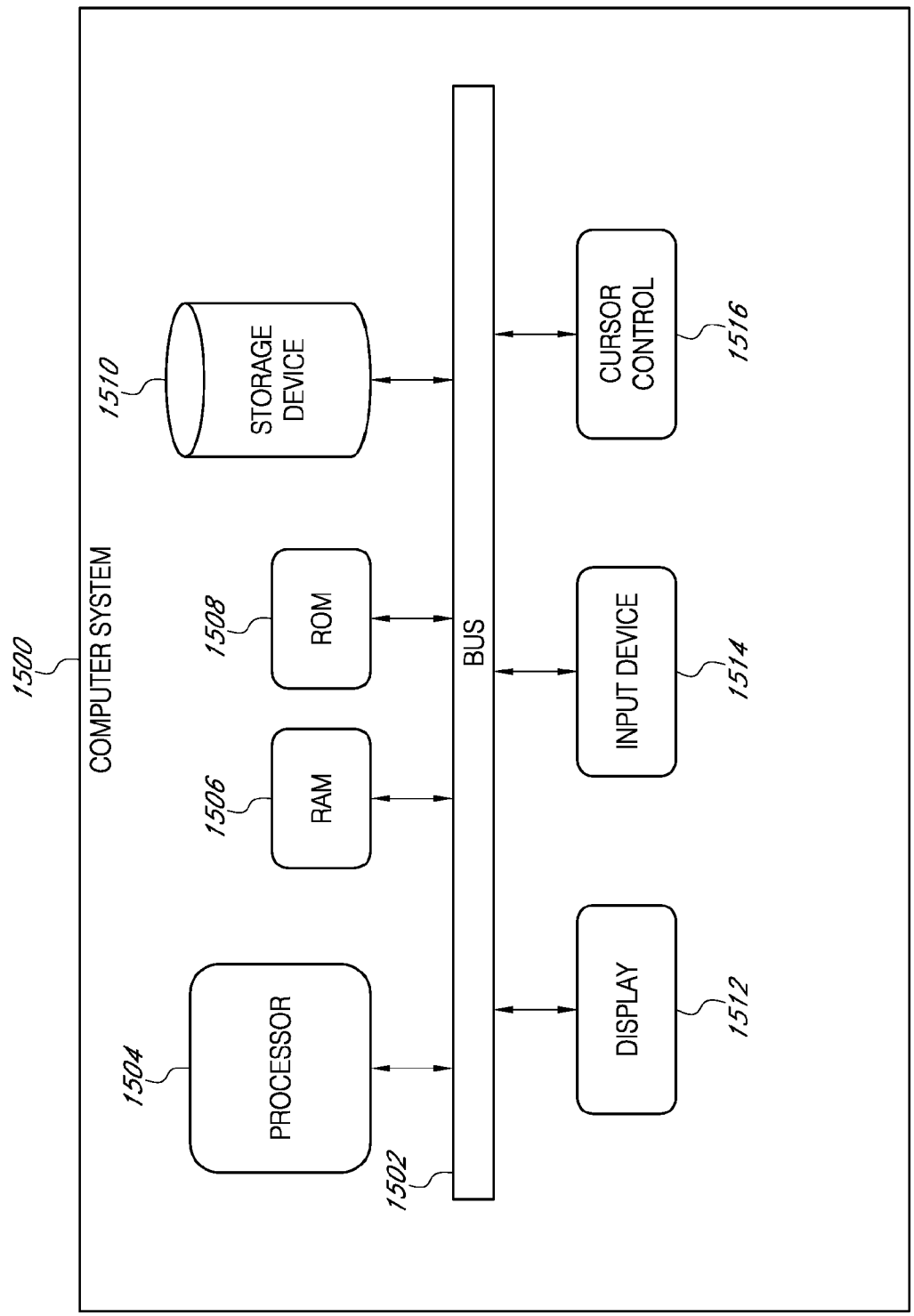
FIG. 15 is a block diagram that illustrates a computer system, upon which embodiments of the present teachings may be implemented.

FIG. 15 is a block diagram that illustrates a computer system 1500, upon which embodiments of the present teachings may be implemented. In various embodiments of the present teachings, computer system 1500 can include a bus 1502 or other communication mechanism for communicating information, and a processor 1504 coupled with bus 1502 for processing information. In various embodiments, computer system 1500 can also include a memory, which can be a random access memory (RAM) 1506 or other dynamic storage device, coupled to bus 1502 for determining instructions to be executed by processor 1504. Memory also can be used for storing temporary variables or other intermediate information during execution of instructions to be executed by processor 1504. In various embodiments, computer system 1500 can further include a read only memory (ROM) 1508 or other static storage device coupled to bus 1502 for storing static information and instructions for processor 1504. A storage device 1510, such as a magnetic disk or optical disk, can be provided and coupled to bus 1502 for storing information and instructions.

In various embodiments, computer system 1500 can be coupled via bus 1502 to a display 1512, such as a cathode ray tube (CRT) or liquid crystal display (LCD), for displaying information to a computer user. An input device 1514, including alphanumeric and other keys, can be coupled to bus 1502 for communicating information and command selections to processor 1504. Another type of user input device is a cursor control 1516, such as a mouse, a trackball or cursor direction keys for communicating direction information and command selections to processor 1504 and for controlling cursor movement on display 1512. This input device 1514 typically has two degrees of freedom in two axes, a first axis (i.e., x) and a second axis (i.e., y), that allows the device to specify positions in a plane. However, it should be understood that input devices 1514 allowing for 3 dimensional (x, y and z) cursor movement are also contemplated herein.

Consistent with certain implementations of the present teachings, results can be provided by computer system 1500 in response to processor 1504 executing one or more sequences of one or more instructions contained in memory 1506. Such instructions can be read into memory 1506 from another computer-readable medium or computer-readable storage medium, such as storage device 1510. Execution of the sequences of instructions contained in memory 1506 can cause processor 1504 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1504 for execution. Such a medium can take many forms, including but not limited to, non-volatile media, volatile media, and transmission media. Examples of non-volatile media can include, but are not limited to, optical, solid state, magnetic disks, such as storage device 1510. Examples of volatile media can include, but are not limited to, dynamic memory, such as memory 1506. Examples of transmission media can include, but are not limited to, coaxial cables, copper wire, and fiber optics, including the wires that comprise bus 1502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1504 of computer system 1500 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

VIII. Exemplary Embodiments

Various exemplary embodiments are described herein.

In one or more embodiments, a method is provided for training a neural network to predict at least one pharmacokinetic parameter of an agent. One or more processors receive a simulation parameter for a compartmental-based pharmacokinetic model. The one or more processors generate a simulated training data collection using the compartmental-based pharmacokinetic model. The simulated training data collection comprises a simulated time-series concentration dataset of one or more agents and a simulated value for a pharmacokinetic parameter that corresponds to the simulated time-series concentration dataset. The compartmental-based pharmacokinetic model is encoded with the received simulation parameters. The one or more processors then train a neural network with the simulated training data collection.

In one or more embodiments, a system for training a neural network to predict a pharmacokinetic parameter value of an agent is disclosed. The system includes a data store, a computing device, and a display system. The data store stores simulation parameters for a compartmental-based pharmacokinetic model. The computing device is communicatively connected to the data store and hosts a pharmacokinetic data simulation engine and a pharmacokinetic prediction engine. The pharmacokinetic data simulation engine is configured to use the compartmental-based pharmacokinetic models to generate a simulated training data collection. The simulated training data collection comprises a simulated time-series concentration dataset of one or more agents and a simulated value for a pharmacokinetic parameter that corresponds to the simulated time-series concentration dataset. The pharmacokinetic prediction engine is configured to train a neural network using the simulated training data collection.

In one or more embodiments, a system for predicting a pharmacokinetic parameter value of an agent administered to a subject comprises a data store for storing a time-series concentration dataset of an agent obtained from a subject; a computing device communicatively connected to the data store that comprises: a pharmacokinetic prediction engine configured to train a neural network and predict a pharmacokinetic parameter value based on the time-series concentration dataset of the agent obtained from the subject, wherein the neural network was trained using a simulated training data collection comprising a plurality of simulated time-series concentration datasets of one or more agents as well as corresponding simulated pharmacokinetic parameter values; and a display communicatively connected to the computing device and configured to display a report containing the predicted pharmacokinetic parameter value.

In one or more embodiments, a non-transitory computer-readable medium storing computer instructions for predicting at least one pharmacokinetic parameter value of an agent administered to a subject comprising: training, by one or more processors, a neural network based on a simulated training data collection, the simulated training data collection comprising a simulated time-series concentration dataset and a simulated value for a pharmacokinetic parameter that corresponds to the simulated time-series concentration dataset; receiving, by the one or more processors, a time-series concentration dataset of the agent obtained from a subject; and predicting, by the one or more processors, a value for the pharmacokinetic parameter using the time-series concentration dataset and the neural network that has been trained.

In one or more embodiments, a non-transitory computer-readable medium storing computer instructions for training neural network to predict at least one pharmacokinetic parameter of an agent, comprising: receiving a simulation parameter for a compartmental-based pharmacokinetic model; generating a simulated training data collection using the compartmental-based pharmacokinetic model, wherein the simulated training data collection comprises a simulated time-series concentration dataset of one or more agents and a simulated value for a pharmacokinetic parameter that corresponds to the simulated time-series concentration dataset; encoding the compartmental-based pharmacokinetic model with the received simulation parameters; and training a neural network with the simulated training data collection.

In one or more embodiments, a non-transitory computer-readable medium storing computer instructions for predicting at least one pharmacokinetic parameter of an agent administered to a subject, comprising: receiving, by one or more processors, a time-series concentration dataset of the agent obtained from a subject; and predicting, by the one or more processors, a value for a pharmacokinetic parameter based on the time-series concentration dataset and a neural network that has been trained using a simulated training data collection.

In one or more embodiments, the neural network of one or more of the exemplary embodiments described herein is a convolutional neural network in some embodiments.

In one or more embodiments, the simulation parameter of one or more of the exemplary embodiments described herein is a class of agent being simulated.

In one or more embodiments, the agent of one or more of the exemplary embodiments described herein is one of a small molecule therapeutic or a biologic.

In one or more embodiments, the simulation parameter of one or more of the exemplary embodiments described herein is a dosing scheme for the agent.

In one or more embodiments, the dosing scheme of one or more of the exemplary embodiments described herein is one of an intravenous administration of the agent or an oral administration of the agent.

In one or more embodiments, the compartmental-based pharmacokinetic model of one or more of the exemplary embodiments described herein comprises at least one of a one-compartment model, a two-compartment model, or a Michaelis-Menten model.

In one or more embodiments, the data store and the computing device of one or more of the exemplary embodiments described herein are part of an integrated apparatus.

In one or more embodiments, the data store of one or more of the exemplary embodiments described herein is hosted by a different device than the computing device of one or more of the exemplary embodiments described herein.

In one or more embodiments, the data store and the computing device of one or more of the exemplary embodiments described herein are part of a distributed network system.

IX. Additional Considerations

It should be appreciated that the methodologies described herein flow charts, diagrams and accompanying disclosure can be implemented using computer system 1300 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1100, whereby processor 1104 would execute the analyses and determinations provided by these engines, subject to instructions provided by any one of, or a combination of, memory components 1106/1108/1110 and user input provided via input device 1114.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

What is claimed is:

1. A system for predicting at least one pharmacokinetic parameter of an agent administered to a subject, comprising: one or more processors; and a non-transitory memory coupled to the processors comprising instructions executable by the processors, the processors operable when executing the instructions to:
access a blood sample obtained from the subject;
generate a time-series concentration data associated with the agent based on an analysis of the blood sample by a sample analyzer coupled to the system;
execute a neural network on the time-series concentration data to predict a value for the at least one pharmacokinetic parameter,
wherein predicting the value for the at least one pharmacokinetic parameter comprises predicting the value based on weights of a plurality of nodes across a plurality of layers associated with the neural network and the time-series concentration data,
wherein the neural network has been trained using a simulated training data collection comprising a plurality of simulated time-series concentration data and a plurality of simulated values for the at least one pharmacokinetic parameter that correspond to the plurality of simulated time-series concentration data, respectively, and
where the simulated training data collection is generated based on running simulations by one or more compartment-based pharmacokinetic models based on customized model parameters associated with the one or more compartment-based pharmacokinetic models;
and
display a report containing the value predicted for the at least one pharmacokinetic parameter.

2. The system of claim 1, wherein the one or more compartmental-based pharmacokinetic models comprise at least one of a one-compartment model, a two-compartment model, or a Michaelis-Menten model.

3. The system of claim 1, wherein the neural network comprises a convolutional neural network.

4. The system of claim 1, wherein the agent comprises a small molecule therapeutic or a biologic.

5. The system of claim 1, wherein the processors are further operable when executing the instructions to store the time-series concentration data in a data store, and wherein the data store and the system are part of an integrated apparatus.

6. The system of claim 1, wherein the processors are further operable when executing the instructions to store the time-series concentration data in a data store, and wherein the data store is hosted by a different device than the system.

7. A method for predicting at least one pharmacokinetic parameter of an agent administered to a subject, comprising:
accessing a blood sample obtained from the subject;
generating, by a sample analyzer coupled to one or more processors, a time-series concentration data associated with the agent based on an analysis of the blood sample; and
executing, by the one or more processors, a neural network on the time-series concentration data to predict a value for the at least one pharmacokinetic parameter,
wherein predicting the value for the at least one pharmacokinetic parameter comprises predicting the value based on weights of a plurality of nodes across a plurality of layers associated with the neural network and the time-series concentration data, wherein the neural network has been trained using a simulated training data collection comprising a plurality of simulated time-series concentration data and a plurality of simulated values for the at least one pharmacokinetic parameter that correspond to the plurality of simulated time-series concentration data, respectively, and where the simulated training data collection is generated based on running simulations by one or more compartment-based pharmacokinetic models based on customized model parameters associated with the one or more compartment-based pharmacokinetic models.

8. The method of claim 7, wherein the neural network is a convolutional neural network.

9. The method of claim 7, wherein the at least one pharmacokinetic parameter comprises at least one of an area under the curve (AUC), a minimum concentration value ($C_{min}$), or a maximum concentration value ($C_{max}$).

10. The method of claim 7, wherein the agent comprises a small molecule therapeutic or a biologic.

11. The method of claim 7, wherein:

training the neural network comprises feeding the simulated training data collection into the neural network through a backpropagation process that adjusts the weights of the plurality of nodes across the plurality of layers associated with the neural network; and generating the simulated training data collection comprises:

setting the customized model parameters associated with the one or more compartment-based pharmacokinetic models, wherein the customized model parameters comprise at least a dosing scheme associated with the agent, a molecular species associated with the agent, and a species associated with the subject;

running the simulations by the one or more compartment-based pharmacokinetic models based on the customized model parameters to generate the plurality of simulated time-series concentration data; and using non-compartment analysis (NCA) to generate the plurality of simulated values for the at least one pharmacokinetic parameter that correspond to the plurality of simulated time-series concentration data, respectively.

* * * * *